(12) United States Patent
Evans et al.

(10) Patent No.: US 7,119,077 B1
(45) Date of Patent: Oct. 10, 2006

(54) MULTIMERIC FORMS OF MEMBERS OF THE STEROID/THYROID SUPERFAMILY OF RECEPTORS WITH THE ULTRASPIRACLE RECEPTOR

(75) Inventors: Ronald M. Evans, La Jolla, CA (US); Michael B. McKeown, San Diego, CA (US); Anthony E. Oro, San Diego, CA (US); William A. Segraves, Ambler, PA (US); Tso-Pang Yao, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 817 days.

(21) Appl. No.: 09/526,298

(22) Filed: Mar. 15, 2000

Related U.S. Application Data

(60) Division of application No. 08/464,514, filed on Jun. 5, 1995, now Pat. No. 6,265,173, which is a division of application No. 07/907,908, filed on Jul. 2, 1992, now abandoned, said application No. 09/526,298 is a continuation-in-part of application No. 07/497,935, filed on Mar. 22, 1990, now abandoned.

(51) Int. Cl.
*C07H 21/04* (2006.01)
*A61K 48/00* (2006.01)

(52) U.S. Cl. ............... 514/44; 435/6; 435/440; 435/375

(58) Field of Classification Search ............... 435/6, 435/440, 375; 514/44
See application file for complete search history.

(56) References Cited

OTHER PUBLICATIONS

Verma et al., "Gene Therapy- Promises, Problems and Prospects" Nature vol. 389:239-242, Sep. 18, 1997.*
Crystal R., "Transfer of Genes to Humans: Early lessons and Obstacles to Success" Science vol. 270:404-410, Oct. 20, 1995.*
Orkin et al., "Report and Recommendations of the Panel to Assess the NIH Investment in Research on Gene Therapy", Dec. 7, 1995.*
Kumar and Chambon, "The Estrogen Receptor Binds Tightly to Its Responsive Element as a Ligand-Induced Homodimer", Cell vol. 55:145-156 (1988).
Tsai et al., "Molecular Interactions of Steroid Hormone Receptor with Its Enhancer Element: Evidence for Receptor Dimer Formation", Cell vol. 55:361-369 (1988).
Murray and Towle, "Identification of Nuclear Factors that Enhance Binding of the Thyroid Hormone Receptor to a Thyroid Hormone Response Element", Molecular Endocrinology vol. 3:1434-1442 (1989).
Glass et al., "Multiple Cell Type-Specific Proteins Differentially Regulate Target Sequence Recognition by the α Retinoic Acid Receptor", Cell vol. 63:729-738 (1990).
Liao et al., "Vitamin D receptor interaction with specific DNA requires a nuclear protein and 1,25-dihydroxyvitamin $D_3$", Proc. Natl. Acad. Sci. USA vol. 87:9751-9755 (1990).
Leid et al., "Purification, Cloning and RXR Identity of the HeLa Cell Factor with Which RAR or TR Heterodimerizes to Bind Target Sequences Efficiently", Cell vol. 68:377-395 (1992).
Yu et al., RXRB: A Coregulator That Enhances Binding of Retinoic Acid, Thyroid Hormone, and Vitamin D Receptors to Their Cognate Response Elements, Cell vol. 67:1251-1266 (1991).
Kliewer et al., "Retinoid X receptor interacts with nuclear receptors in retinoic acid, thyroid hormone and vitamin $D_3$ signalling", Nature vol. 355:446-449 (1992).
Zhang et al., "Retinoid X receptor is an auxiliary protein for thyroid hormone and retinoic acid receptors", Nature vol. 355:441-446 (1992).
Cherbas et al., "The Action of Ecdysone in Imaginal Discs and KcCells of *Drosophila melanogaster*" Biosynthesis, metabolism and mode of action of invertebrate hormones, (ed. J Hoffman & M. Porchet pp. 305-322 Springer-Verlag, Berlin, 1984).
Koelle et al., "The *Drosophila* EcR Gene Encodes an Ecdysone Receptor, a New Member of the Steroid Receptor Superfamily", Cell vol. 67:59-77 (1991).
Kunkel, Thomas A., "Rapid and efficient site-specific mutagenesis without phenotypic selection", Proc. Natl. Acad. Sci. USA vol. 82:488-492 (1985).
Soeller et al., "*In vitro* transcription of the *Drosophila engrailed* gene", Genes & Development vol. 2:68-81 (1988).
Kliewer et al., "Convergence of 9-cis retinoic acid and peroxisome proliferator signalling pathways through heterodimer formation of their receptors", Nature vol. 358:771-774 (1992).
Noda et al., "Identification of a DNA sequence responsible for binding of the 1,25-dihydroxyvitamin $D_3$ receptor and 1,25-dihydroxyvitamin $D_3$ enhancement of mouse secreted phosphoprotein 1 (Spp-1 or osteopontin) gene expression", Proc. Natl. Acad. Sci. USA vol. 87:9995-9999 (1990).

(Continued)

*Primary Examiner*—Sean McGarry
(74) *Attorney, Agent, or Firm*—Foley & Lardner; Stephen E. Reiter

(57) ABSTRACT

In accordance with the present invention, it has been discovered that various members of the steroid/thyroid superfamily of receptors can interact with the insect-derived ultraspiracle receptor, to form multimeric species. Accordingly, the interaction of at least one member of the steroid/thyroid superfamily of receptors with at least the dimerization domain of the ultraspiracle receptor modulates the ability of said member of the steroid/thyroid superfamily of receptors to transactivate transcription of genes maintained under hormone expression control in the presence of the cognate ligand for said member of the superfamily.

20 Claims, 2 Drawing Sheets

OTHER PUBLICATIONS

Sap et al., "Repression of transcription mediated at a thyroid hormone response element by the v-erb-A oncogene product", Nature vol. 340:242-244 (1989).

Forman et al., "A Domain Containing Leucine-Zipper-Like Motifs Mediate Novel in vivo Interactions between the Thyroid Hormone and Retinoid Acid Receptors", Molecular Endocrinology vol. 3:1610-1626 (1989).

Fawell et al., "Characterization and Colocalization of Steroid Binding and Dimerization Activities in the Mouse Estrogen Receptor", Cell vol. 60:953-962 (1990).

Riddihough and Pelham, "An ecdysone response element in the Drosophila hsp27 promoter", The EMBO Journal vol. 6:3729-3734 (1987).

Richards, Geoff, "The Radioimmune Assay of Ecdysteroid Titres in Drosophila melanogaster", Molecular and Celluar Endocrinology vol. 21:181-197 (1981).

Oro et al., The Drosophila retinoid X receptor homolog ultraspiracle functions in both female reproduction and eye morphogenesis, Development vol. 115:449-462 (1992).

Yang et al., "Characterization of DNA binding and retinoic acid binding properties of retinoic acid receptor", Proc. Natl. Acad. Sci. USA vol. 88:3559-3563 (1991).

Damm et al., "Protein encoded by v-erbA functions as a thyroid-hormone receptor antagonist", Nature vol. 339:593-597 (1989).

Sucov et al., "Characterization of an autoregulated response element in the mouse retinoic acid receptor type B gene", Proc. Natl. Acad. Sci. USA vol. 87:5392-5396 (1990).

de The et al., "Identification of a retinoic acid responsive element in the retinoic acid receptor B gene", Nature vol. 343:177-180 (1990).

Thompson and Evans, "Trans-activation by thyroid hormone receptors: Functional parallels with steroid hormone receptors", Proc. Natl. Acad. Sci. USA vol. 86:3494-3498 (1989).

Issemann and Green, "Activation of a member of the steroid hormone receptor superfamily by peroxisome proliferators", Nature vol. 347:645-650 (1990).

Oro et al., "Relationship between the product of the Drosophila ultraspiracle locus and the vertebrate retinoid X receptor", Nature vol. 347:298-301 (1990).

Evans, Ronald M., "The Steroid and Thyroid Hormone Receptor Superfamily", Science vol. 240:889-895 (1988).

Vaughan et al., "Detection and Purification of Inhibin Using Antisera Generated against Synthetic Peptide Fragments", Methods in Enzymology vol. 168:588-617 (1989).

Mangelsdorf et al., "Nuclear receptor that identifies a novel retinoic acid response pathways", Nature vol. 345:224-229 (1990).

Sladek et al., "Liver-enriched transcription factor HNF—4 is a novel member of the steroid hormone receptor superfamily", Genes & Development vol. 4:2353-2365 (1990).

Miyajima et al., "Identification of two novel members of erbA superfamily by molecular cloning: the gene products of the two are highly related to each other", Nucleic Acids Research vol. 16:11057-11074 (1988).

Wang et al., "COUP transcription factor is a member of the steroid receptor superfamily", Nature vol. 340:163-166 (1989).

Mlodzik et al., "The Drosophila seven-up Gene, a Member of the Steroid Receptor Gene Superfamily, Controls Photoreceptor Cell Fates", Cell vol. 60:211-224 (1990).

Ladias and Karathanasis, "Regulation of the Apolipoprotein AI Gene by ARP-1, a Novel Member of the Steroid Receptor Superfamily", Science vol. 251:561-565 (1991).

Umesono et al., "Direct Repeats as Selective Response Elements for the Thyroid Hormone, Retinoic Acid, and Vitamin $D_3$ Receptors", Cell vol. 65:1255-1266 (1991).

Hollenberg and Evans, "Multiple and Cooperative trans-Activation Domains of the Human Glucocorticoid Receptor", Cell vol. 55:899-906 (1988).

Giguere et al., "Identification of a receptor for the morphogen retinoic acid", Nature vol. 330:624-629 (1987).

Umesono et al., "Retinoic acid and thyroid hormone induce gene expression through a common responsive element", Nature vol. 336:262-265 (1988).

Cherbas et al., "Identification of ecdysone response elements by analysis of the Drosophila Eip28/29 gene", Genes & Development vol. 5:120-131 (1991).

* cited by examiner

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
        (A) LENGTH: 2304 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 163..1701

(xi) SEQUENCE DESCRIPTION: SEQ ID NO:1:

```
GGACACGGTG GCGTTGGCAA AGTGAAACCC CAACAGAGAG GCGAAAGCGA GCCAAGACAC         60

ACCACATACA CACGAAGAGA ACGAGCAAGA AGAAACCGGT AGGCGGAGGA GGCGCTGCCC        120

CCAGTTCCTC CAATATACCC AGCACCACAT CACAAGCCCA GG ATG GAC AAC TGC          174
                                              Met Asp Asn Cys
                                               1

GAC CAG GAC GCC AGC TTT CGG CTG AGC CAC ATC AAG GAG GAG GTC AAG         222
Asp Gln Asp Ala Ser Phe Arg Leu Ser His Ile Lys Glu Glu Val Lys
 5                  10                  15                  20

CCG GAC ATC TCG CAG CTG AAC GAC AGC AAC AAC AGC AGC TTT TCG CCC         270
Pro Asp Ile Ser Gln Leu Asn Asp Ser Asn Asn Ser Ser Phe Ser Pro
            25                  30                  35

AAG GCC GAG AGT CCC GTG CCC TTC ATG CAG GCC ATG TCC ATG GTC CAC         318
Lys Ala Glu Ser Pro Val Pro Phe Met Gln Ala Met Ser Met Val His
        40                  45                  50

GTG CTG CCC GGC TCC AAC TCC GCC AGC TCC AAC AAC AAC AGC GCT GGA         366
Val Leu Pro Gly Ser Asn Ser Ala Ser Ser Asn Asn Asn Ser Ala Gly
    55                  60                  65

GAT GCC CAA ATG GCG CAG GCG CCC AAT TCG GCT GGA GGC TCT GCC GCC         414
Asp Ala Gln Met Ala Gln Ala Pro Asn Ser Ala Gly Gly Ser Ala Ala
 70                  75                  80

GCT GCA GTC CAG CAG CAG TAT CCG CCT AAC CAT CCG CTG AGC GGC AGC         462
Ala Ala Val Gln Gln Gln Tyr Pro Pro Asn His Pro Leu Ser Gly Ser
 85                  90                  95                 100

AAG CAC CTC TGC TCT ATT TGC GGG GAT CGG GCC AGT GGC AAG CAC TAC         510
Lys His Leu Cys Ser Ile Cys Gly Asp Arg Ala Ser Gly Lys His Tyr
                105                 110                 115

GGC GTG TAC AGC TGT GAG GGC TGC AAG GGC TTC TTT AAA CGC ACA GTG         558
Gly Val Tyr Ser Cys Glu Gly Cys Lys Gly Phe Phe Lys Arg Thr Val
            120                 125                 130

CGC AAG GAT CTC ACA TAC GCT TGC AGG GAG AAC CGC AAC TGC ATC ATA         606
Arg Lys Asp Leu Thr Tyr Ala Cys Arg Glu Asn Arg Asn Cys Ile Ile
        135                 140                 145

GAC AAG CGG CAG AGG AAC CGC TGC CAG TAC TGC CGC TAC CAG AAG TGC         654
Asp Lys Arg Gln Arg Asn Arg Cys Gln Tyr Cys Arg Tyr Gln Lys Cys
    150                 155                 160

CTA ACC TGC GGC ATG AAG CGC GAA GCG GTC CAG GAG GAG CGT CAA CGC         702
Leu Thr Cys Gly Met Lys Arg Glu Ala Val Gln Glu Glu Arg Gln Arg
165                 170                 175                 180

GGC GCC CGC AAT GCG GCG GGT AGG CTC AGC GCC AGC GGA GGC GGC AGT         750
Gly Ala Arg Asn Ala Ala Gly Arg Leu Ser Ala Ser Gly Gly Gly Ser
                185                 190                 195

AGC GGT CCA GGT TCG GTA GGC GGA TCC AGC TCT CAA GGC GGA GGA GGA         798
Ser Gly Pro Gly Ser Val Gly Gly Ser Ser Ser Gln Gly Gly Gly Gly
            200                 205                 210

GGA GGC GGC GTT TCT GGC GGA ATG GGC AGC GGC AAC GGT TCT GAT GAC         846
Gly Gly Gly Val Ser Gly Gly Met Gly Ser Gly Asn Gly Ser Asp Asp
        215                 220                 225
```

|  |  |
|---|---|
| TTC ATG ACC AAT AGC GTG TCC AGG GAT TTC TCG ATC GAG CGC ATC ATA<br>Phe Met Thr Asn Ser Val Ser Arg Asp Phe Ser Ile Glu Arg Ile Ile<br>230                    235                    240 | 894 |
| GAG GCC GAG CAG CGA GCG GAG ACC CAA TGC GGC GAT CGT GCA CTG ACG<br>Glu Ala Glu Gln Arg Ala Glu Thr Gln Cys Gly Asp Arg Ala Leu Thr<br>245                    250                    255                    260 | 942 |
| TTC CTG CGC GTT GGT CCC TAT TCC ACA GTC CAG CCG GAC TAC AAG GGT<br>Phe Leu Arg Val Gly Pro Tyr Ser Thr Val Gln Pro Asp Tyr Lys Gly<br>                    265                    270                    275 | 990 |
| GCC GTG TCG GCC CTG TGC CAA GTG GTC AAC AAA CAG CTC TTC CAG ATG<br>Ala Val Ser Ala Leu Cys Gln Val Val Asn Lys Gln Leu Phe Gln Met<br>              280                    285                    290 | 1038 |
| GTC GAA TAC GCG CGC ATG ATG CCG CAC TTT GCC CAG GTG CCG CTG GAC<br>Val Glu Tyr Ala Arg Met Met Pro His Phe Ala Gln Val Pro Leu Asp<br>295                    300                    305 | 1086 |
| GAC CAG GTG ATT CTG CTG AAA GCC GCT TGG ATC GAG CTG CTC ATT GCG<br>Asp Gln Val Ile Leu Leu Lys Ala Ala Trp Ile Glu Leu Leu Ile Ala<br>310                    315                    320 | 1134 |
| AAC GTG GCC TGG TGC AGC ATC GTT TCG CTG GAT GAC GGC GGT GCC GGC<br>Asn Val Ala Trp Cys Ser Ile Val Ser Leu Asp Asp Gly Gly Ala Gly<br>325                    330                    335                    340 | 1182 |
| GGC GGG GGC GGT GGA CTA GGC CAC GAT GGC TCC TTT GAG CGA CGA TCA<br>Gly Gly Gly Gly Gly Leu Gly His Asp Gly Ser Phe Glu Arg Arg Ser<br>                    345                    350                    355 | 1230 |
| CCG GGC CTT CAG CCC CAG CAG CTG TTC CTC AAC CAG AGC TTC TCG TAC<br>Pro Gly Leu Gln Pro Gln Gln Leu Phe Leu Asn Gln Ser Phe Ser Tyr<br>              360                    365                    370 | 1278 |
| CAT CGC AAC AGT GCG ATC AAA GCC GGT GTG TCA GCC ATC TTC GAC CGC<br>His Arg Asn Ser Ala Ile Lys Ala Gly Val Ser Ala Ile Phe Asp Arg<br>                    375                    380                    385 | 1326 |
| ATA TTG TCG GAG CTG AGT GTA AAG ATG AAG CGG CTG AAT CTC GAC CGA<br>Ile Leu Ser Glu Leu Ser Val Lys Met Lys Arg Leu Asn Leu Asp Arg<br>390                    395                    400 | 1374 |
| CGC GAG CTG TCC TGC TTG AAG GCC ATA ATA CTG TAC AAC CCG GAC ATA<br>Arg Glu Leu Ser Cys Leu Lys Ala Ile Ile Leu Tyr Asn Pro Asp Ile<br>405                    410                    415                    420 | 1422 |
| CGC GGG ATC AAG AGC CGG GCG GAG ATC GAG ATG TGC CGC GAG AAG GTG<br>Arg Gly Ile Lys Ser Arg Ala Glu Ile Glu Met Cys Arg Glu Lys Val<br>                    425                    430                    435 | 1470 |
| TAC GCT TGC CTG GAC GAG CAC TGC CGC CTG GAA CAT CCG GGC GAC GAT<br>Tyr Ala Cys Leu Asp Glu His Cys Arg Leu Glu His Pro Gly Asp Asp<br>              440                    445                    450 | 1518 |
| GGA CGC TTT GCG CAA CTG CTG CTG CGT CTG CGC CGC TTT GCG ATC GAT<br>Gly Arg Phe Ala Gln Leu Leu Leu Arg Leu Arg Arg Phe Ala Ile Asp<br>455                    460                    465 | 1566 |
| CAG CCT GAA GTG CCA GGA TCA CCT GTT CCT CTT CCG CAT TAC CAG CGA<br>Gln Pro Glu Val Pro Gly Ser Pro Val Pro Leu Pro His Tyr Gln Arg<br>470                    475                    480 | 1614 |
| CCG GCC GCT GGA GGA GCT CTT TCT CGA GCA GCT GGA GGC GCC GCC GCC<br>Pro Ala Ala Gly Gly Ala Leu Ser Arg Ala Ala Gly Gly Ala Ala Ala<br>485                    490                    495                    500 | 1662 |
| ACC CGG CCT GGC GAT GAA ACT GGA GTA GGG TCC CGA CTC TAAAGTCGCC<br>Thr Arg Pro Gly Asp Glu Thr Gly Val Gly Ser Arg Leu<br>                    505                    510 | 1711 |
| CCCGTTCTCC ATCCGAAAAA TGTTTCATTG TGATTGCGTT TGTTTGCATT TCTCCTCTCT | 1771 |
| ATCCCTACAA AAGCCCCCTA ATATTACGCA AAATGTGTAT GTAATTGTTT ATTTTTTTTT | 1831 |
| TATTACCTAA TATTATTATT ATTATTGATA TAGAAAATGT TTTCCTTAAG ATGAAGATTA | 1891 |
| GCCTCCTCGA CGTTTATGTC CCAGTAAACG AAAAACAAAC AAAATCCAAA ACTTGAAAAG | 1951 |

```
AACACAAAAC ACGAACGAGA AAATGCACAC AAGCAAAGTA AAAGTAAAAG TTAAACTAAA      2011

GCTAAACGAG TAAAGATATT AAAATAACGG TTAAAATTAA TGCATAGTTA TGATCTACAG      2071

ACGTATGTAA ACATACAAAT TCAGCATAAA TATATATGTC AGCAGGCGCA TATCTGCGGT      2131

GCTGGCCCCG TTCTAAACCA ATTGTAATTA CTTTTTAACA TAAATTTACC CAAAACGTTA      2191

TCAATTAGAT GCGAGATACA AAAATCACCG ACGAAAACCA ACAAAATATA TCTATGTATA      2251

AAAAATATAA GCTGCATAAC AAAAAAAAAA AAAAAAAAAA AAAAAAAAAA AAA            2304
```

(2) INFORMATION FOR SEQ ID NO:2:

(i) SEQUENCE CHARACTERISTICS:
        (A) LENGTH: 513 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Asn Cys Asp Gln Asp Ala Ser Phe Arg Leu Ser His Ile Lys
 1               5                  10                  15

Glu Glu Val Lys Pro Asp Ile Ser Gln Leu Asn Asp Ser Asn Asn Ser
                20                  25                  30

Ser Phe Ser Pro Lys Ala Glu Ser Pro Val Pro Phe Met Gln Ala Met
            35                  40                  45

Ser Met Val His Val Leu Pro Gly Ser Asn Ser Ala Ser Ser Asn Asn
        50                  55                  60

Asn Ser Ala Gly Asp Ala Gln Met Ala Gln Ala Pro Asn Ser Ala Gly
65                  70                  75                  80

Gly Ser Ala Ala Ala Val Gln Gln Gln Tyr Pro Pro Asn His Pro
                85                  90                  95

Leu Ser Gly Ser Lys His Leu Cys Ser Ile Cys Gly Asp Arg Ala Ser
                100                 105                 110

Gly Lys His Tyr Gly Val Tyr Ser Cys Glu Gly Cys Lys Gly Phe Phe
            115                 120                 125

Lys Arg Thr Val Arg Lys Asp Leu Thr Tyr Ala Cys Arg Glu Asn Arg
        130                 135                 140

Asn Cys Ile Ile Asp Lys Arg Gln Arg Asn Arg Cys Gln Tyr Cys Arg
145                 150                 155                 160

Tyr Gln Lys Cys Leu Thr Cys Gly Met Lys Arg Glu Ala Val Gln Glu
                165                 170                 175

Glu Arg Gln Arg Gly Ala Arg Asn Ala Ala Gly Arg Leu Ser Ala Ser
            180                 185                 190

Gly Gly Gly Ser Ser Gly Pro Gly Ser Val Gly Ser Ser Ser Gln
        195                 200                 205

Gly Gly Gly Gly Gly Gly Val Ser Gly Met Gly Ser Gly Asn
    210                 215                 220

Gly Ser Asp Asp Phe Met Thr Asn Ser Val Ser Arg Asp Phe Ser Ile
225                 230                 235                 240

Glu Arg Ile Ile Glu Ala Glu Gln Arg Ala Glu Thr Gln Cys Gly Asp
                245                 250                 255

Arg Ala Leu Thr Phe Leu Arg Val Gly Pro Tyr Ser Thr Val Gln Pro
            260                 265                 270

Asp Tyr Lys Gly Ala Val Ser Ala Leu Cys Gln Val Val Asn Lys Gln
        275                 280                 285
```

```
Leu Phe Gln Met Val Glu Tyr Ala Arg Met Met Pro His Phe Ala Gln
290                 295                 300
Val Pro Leu Asp Asp Gln Val Ile Leu Leu Lys Ala Ala Trp Ile Glu
305                 310                 315                 320
Leu Leu Ile Ala Asn Val Ala Trp Cys Ser Ile Val Ser Leu Asp Asp
                325                 330                 335
Gly Gly Ala Gly Gly Gly Gly Gly Leu Gly His Asp Gly Ser Phe
            340                 345                 350
Glu Arg Arg Ser Pro Gly Leu Gln Pro Gln Gln Leu Phe Leu Asn Gln
            355                 360                 365
Ser Phe Ser Tyr His Arg Asn Ser Ala Ile Lys Ala Gly Val Ser Ala
370                 375                 380
Ile Phe Asp Arg Ile Leu Ser Glu Leu Ser Val Lys Met Lys Arg Leu
385                 390                 395                 400
Asn Leu Asp Arg Arg Glu Leu Ser Cys Leu Lys Ala Ile Ile Leu Tyr
                405                 410                 415
Asn Pro Asp Ile Arg Gly Ile Lys Ser Arg Ala Glu Ile Glu Met Cys
                420                 425                 430
Arg Glu Lys Val Tyr Ala Cys Leu Asp Glu His Cys Arg Leu Glu His
            435                 440                 445
Pro Gly Asp Asp Gly Arg Phe Ala Gln Leu Leu Leu Arg Leu Arg Arg
450                 455                 460
Phe Ala Ile Asp Gln Pro Glu Val Pro Gly Ser Pro Val Pro Leu Pro
465                 470                 475                 480
His Tyr Gln Arg Pro Ala Ala Gly Gly Ala Leu Ser Arg Ala Ala Gly
            485                 490                 495
Gly Ala Ala Ala Thr Arg Pro Gly Asp Glu Thr Gly Val Gly Ser Arg
            500                 505                 510
Leu
```

(2) INFORMATION FOR SEQ ID NO:3:

(i) SEQUENCE CHARACTERISTICS:
    (A) LENGTH: 71 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:3:

```
Cys Xaa Xaa Cys Xaa Xaa Asp Xaa Ala Xaa Gly Xaa Tyr Xaa Xaa Xaa
1               5                   10                  15
Xaa Cys Xaa Xaa Cys Lys Xaa Phe Phe Xaa Arg Xaa Xaa Xaa Xaa Xaa
            20                  25                  30
Xaa Xaa Xaa Xaa Xaa Xaa Cys Xaa Xaa Xaa Xaa Xaa Xaa Xaa Xaa Cys
            35                  40                  45
Xaa Xaa Xaa Lys Xaa Xaa Arg Xaa Xaa Cys Xaa Xaa Cys Arg Xaa Xaa
50                  55                  60
Lys Cys Xaa Xaa Xaa Gly Met
65                  70
```

(2) INFORMATION FOR SEQ ID NO:4:

(i) SEQUENCE CHARACTERISTICS:
    (A) LENGTH: 15 base pairs
    (B) TYPE: nucleic acid
    (C) STRANDEDNESS: single (D) TOPOLOGY: linear (xi) SEQUENCE DESCRIPTION: SEQ ID NO:4:

AGGTCAAGGA GGTCA                                                15

(2) INFORMATION FOR SEQ ID NO:5:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:5:

GGGTGAATGA GGACA                                                15

(2) INFORMATION FOR SEQ ID NO:6:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:6:

GGGTGAACGG GGGCA                                                15

(2) INFORMATION FOR SEQ ID NO:7:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:7:

GGTTCACGAG GTTCA                                                15

(2) INFORMATION FOR SEQ ID NO:8:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:8:

AGGTCACAGG AGGTCA                                               16

(2) INFORMATION FOR SEQ ID NO:9:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:9:

AGGTGACAGG AGGTCA                                               16

(2) INFORMATION FOR SEQ ID NO:10:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:10:

AGGTGACAGG AGGACA                                                             16

(2) INFORMATION FOR SEQ ID NO:11:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:11:

GGGTTAGGGG AGGACA                                                             16

(2) INFORMATION FOR SEQ ID NO:12:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:12:

GGGTCATTTC AGGTCC                                                             16

(2) INFORMATION FOR SEQ ID NO:13:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:13:

AGGTCACCAG GAGGTCA                                                            17

(2) INFORMATION FOR SEQ ID NO:14:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:14:

AGGTGAACAG GAGGTCA                                                            17

(2) INFORMATION FOR SEQ ID NO:15:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:15:

GGTTCACCGA AAGTTCA                                                            17

(2) INFORMATION FOR SEQ ID NO:16:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:16:

GGTTCACCGA AAGTTCA                                                      17

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:17:

AGGTCACTGA CAGGGCA                                                      17

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:18:

GGGTCATTCA GAGTTCA                                                      17

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:19:

AAGCTTAAGG GTTCACCGAA AGTTCACTCA GCTT                                   34

(2) INFORMATION FOR SEQ ID NO:20:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:20:

AAGCTTAAGG GTTCACCGAA AGTTCACTCG CATAGCTT                               38

(2) INFORMATION FOR SEQ ID NO:21:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:21:

AAGCTTAAGG GTTCACCGAA AGTTCACTCG CATATATTAG CTT                         43

(2) INFORMATION FOR SEQ ID NO:22:

(i) SEQUENCE CHARACTERISTICS:
        (A) LENGTH: 62 base pairs
        (B) TYPE: nucleic acid
        (C) STRANDEDNESS: single
        (D) TOPOLOGY: unknown (xi) SEQUENCE DESCRIPTION: SEQ ID NO:22:

AGCTCGATGG ACAAGTGCAT TGAACCCTTG AGCTACCTGT TCACGTAACT TGGGAACTTC    60

GA    62

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (xi) SEQUENCE DESCRIPTION: SEQ ID NO:23:

CCTGCGCCAC GGCGGCCGCC GGAGCTGTGC CTG    33

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (xi) SEQUENCE DESCRIPTION: SEQ ID NO:24:

GTGGGTATGC GCCTCGAGTG CGTCGTCCC    29

(2) INFORMATION FOR SEQ ID NO:25:

(i) SEQUENCE CHARACTERISTICS:
        (A) LENGTH: 13 base pairs
        (B) TYPE: nucleic acid
        (C) STRANDEDNESS: single
        (D) TOPOLOGY: unknown (xi) SEQUENCE DESCRIPTION: SEQ ID NO:25:

AGGACAAAGG TCA    13

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: double
        (D) TOPOLOGY: unknown (xi) SEQUENCE DESCRIPTION: SEQ ID NO:26:

ATTGGACAAG TGCATTGAAC CCTTGTCTCT    30

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: double
        (D) TOPOLOGY: unknown (xi) SEQUENCE DESCRIPTION: SEQ ID NO:27:

ATGCTGTGCA TTGAACGTGC TCGA    24

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: double
        (D) TOPOLOGY: unknown

```
       (xi) SEQUENCE DESCRIPTION: SEQ ID NO:28:

ATGAAGTGCA TTGAACCCGC TCGA                                              24

(2) INFORMATION FOR SEQ ID NO:29:

(i) SEQUENCE CHARACTERISTICS:
         (A) LENGTH: 30 base pairs
         (B) TYPE: nucleic acid
         (C) STRANDEDNESS: double
         (D) TOPOLOGY: unknown (xi) SEQUENCE DESCRIPTION: SEQ ID NO:29:

TAAAGGATCT TGACCCCAAT GAACTTCTTA                                        30
```

US 7,119,077 B1

MULTIMERIC FORMS OF MEMBERS OF THE STEROID/THYROID SUPERFAMILY OF RECEPTORS WITH THE ULTRASPIRACLE RECEPTOR

RELATED APPLICATIONS

This application is a divisional of application Ser. No. 08,464,514, filed on Jun. 5, 1995, now U.S. Pat. No. 6,265,173 which is a divisional of application Ser. No. 07/907,908, filed on Jul. 2, 1992, now abandoned; the entire contents of each of which are hereby incorporated by reference herein.

This application is a continuation-in-part of U.S. application Ser. No. 07/497,935, filed Mar. 22, 1990, now abandoned.

FIELD OF THE INVENTION

The present invention relates to interactions between members of the steroid/thyroid superfamily of receptor proteins, novel combinations of various members of the steroid/thyroid superfamily of receptor proteins, and methods of using such combinations.

BACKGROUND OF THE INVENTION

Transcriptional regulation of development and homeostasis in complex eukaryotes, including humans and other mammals, birds, fish, insects, and the like, is controlled by a wide variety of regulatory substances, including steroid and thyroid hormones. These hormones exert potent effects on development and differentiation of phylogenetically diverse organisms. The effects of hormones are mediated by interaction with specific, high affinity binding proteins referred to as receptors.

A number of receptor proteins are known, each specific for steroid hormones [e.g., estrogens (estrogen receptor), progesterones (progesterone receptor), glucocorticoid (glucocorticoid receptor), androgens (androgen receptor), aldosterones (mineralocorticoid receptor), vitamin D (vitamin D receptor)], retinoids (e.g., retinoic acid receptor) or thyroid hormones (e.g., thyroid hormone receptor). Receptor proteins have been found to be distributed throughout the cell population of complex eukaryotes in a tissue specific fashion.

Molecular cloning studies have made it possible to demonstrate that receptors for steroid, retinoid and thyroid hormones are all structurally related and comprise a superfamily of regulatory proteins. These regulatory proteins are capable of modulating specific gene expression in response to hormone stimulation by binding directly to cis-acting elements.

It is known that steroid or thyroid hormones, protected forms thereof, or metabolites thereof, enter cells and bind to the corresponding specific receptor protein, initiating an allosteric alteration of the protein. As a result of this alteration, the complex of receptor and hormone (or metabolite thereof) is capable of binding with high affinity to certain specific sites on chromatin. One of the primary effects of steroid and thyroid hormones is an increase in transcription of a subset of genes in specific cell types.

A number of transcriptional control units which are responsive to members of the steroid/thyroid superfamily of receptors have been identified. These include the mouse mammary tumor virus 5'-long terminal repeat (MTV LTR), responsive to glucocorticoid, aldosterone and androgen hormones; the transcriptional control units for mammalian growth hormone genes, responsive to glucocorticoids, estrogens and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic $\alpha_{2u}$-globulin gene transcriptional control units, responsive to androgens, estrogens, thyroid hormones, and glucocorticoids.

A major obstacle to further understanding and more widespread use of the various members of the steroid/thyroid superfamily of hormone receptors has been a lack of awareness of the possible interactions of various members of the steroid/thyroid superfamily of hormone receptors, and an understanding of the implications of such interactions on the ability of members of the steroid/thyroid superfamily of hormone receptors to exert transcriptional regulation of various physiological processes.

DNA binding studies on the glucocorticoid receptor (GR) and the estrogen receptor (ER) have indicated that these receptors bind to their hormone response elements (HREs) as homodimeric complexes [see, for example, Kumar and Chambon in Cell 55:145–156 (1988) and Tsi et al., in Cell 55:361–369 (1988)]. However, recent biochemical analysis has revealed that some other receptors (including retinoic acid receptor (RAR), thyroid hormone receptor (TR), and the vitamin D receptor (VDR)) can not efficiently bind to cognate response elements as homodimers, but rather require additional factors present in cell nuclear extracts to achieve high affinity DNA binding [see, for example, Murray and Towle in Mol. Endocrinol. 3:1434–1442 (1989), Glass et al., in Cell 63:729–738 (1990), Liao et al., in Proc. Natl. Acad. Sci. USA 87:9751–9755 (1990), and Yang et al., in Proc. Natl. Acad. Sci. USA 88:3559–3563 (1991)].

Several recent reports have identified members of the retinoid X receptor family (RXR; see, for example, Mangelsdorf et al., in Nature 345:224–229 (1990) and Gene Dev. 6:329–344 (1992), and Leid et al., in Cell 68:377–395 (1992)) as factors that can interact with RAR and potentiate DNA binding by forming a novel RAR/RXR heterodimer [see, for example, Yu et al., in Cell 67:1251–1266 (1991), Kliewer et al., in Nature 355:446–449 (1992), Leid et al., supra, and Zhang et al., in Nature 355:441–446 (1992)]. Interestingly, RAR is not the only receptor with which RXR can interact. In fact, RXR has been found to be capable of heterodimerizing with several other members of the nuclear receptor superfamily, including VDR, TR (see Kliewer, et al., supra) and peroxisome proliferator-activated receptor (PPAR; see, for example, Issemann and Green in Nature 347: 645–650 (1990)).

Although the physiological significance of these interactions remains to be definitively determined, the capability of nuclear receptors to heterodimerize suggests the existence of an elaborate network through which distinct nuclear hormone receptor classes are capable of modulating each other's activity. In addition, the possible existence of other factors that can potentially interact with members of the steroid/thyroid superfamily and potentiate DNA binding by forming novel heteromeric species remains to be determined.

BRIEF DESCRIPTION OF THE INVENTION

In accordance with the present invention, we have discovered that various members of the steroid/thyroid superfamily of receptors can combine with the insect derived ultraspiracle receptor (or functional fragments thereof comprising at least the dimerization domain thereof) to form a multimeric complex receptor. Accordingly, the combination of a first receptor species with the ultraspiracle receptor (or a truncated form thereof comprising at least the dimerization domain thereof) is capable of modulating the ability of the first receptor species to trans-activate transcription of genes maintained under steroid hormone or hormone-like expression control in the presence of cognate ligand for said first receptor.

DETAILED DESCRIPTION OF THE INVENTION

In accordance with the present invention, there are provided multimeric receptor species which belong to the steroid/thyroid superfamily of receptors, comprising at least one member of the steroid/thyroid superfamily of receptors, and the ultraspiracle receptor.

As employed herein, the term "dimerization domain(s)" of a member of the steroid/thyroid superfamily of receptors refers to that portion (or portions) of the receptor which is involved in the formation of a given multimeric complex receptor. Dimerization domain(s) typically comprise at least a portion of the carboxy-terminal portion of the receptor (i.e., the carboxy-terminal portion of a receptor with respect to the DNA-binding domain thereof) and/or at least a portion of the DNA binding domain itself. Multiple domains of a given receptor can act in concert as well as independently.

Combinations contemplated by the present invention can broadly be referred to as "multimeric species", which is intended to embrace all of the various oligomeric forms in which members of the steroid/thyroid superfamily of receptors (including fragments thereof comprising the dimerization domains thereof) are capable of associating with at least the dimerization domain of the ultraspiracle receptor. Thus, reference to "combinations" of steroid receptors or "multimeric" forms of steroid receptors with at least the dimerization domain of the ultraspiracle receptor includes heterodimeric combinations of one member of the steroid/thyroid superfamily of receptors (including fragments thereof comprising the dimerization domain thereof) with at least the dimerization domain of the ultraspiracle receptor, heterotrimeric combinations of one or two members of the steroid/thyroid superfamily of receptors (including fragments thereof comprising the dimerization domains thereof) with at least the dimerization domain of the ultraspiracle receptor, heterotetrameric combinations of one, two or three members of the steroid/thyroid superfamily of receptors (including fragments thereof comprising the dimerization domains thereof) with at least the dimerization domain of the ultraspiracle receptor, and the like.

Figure 1:
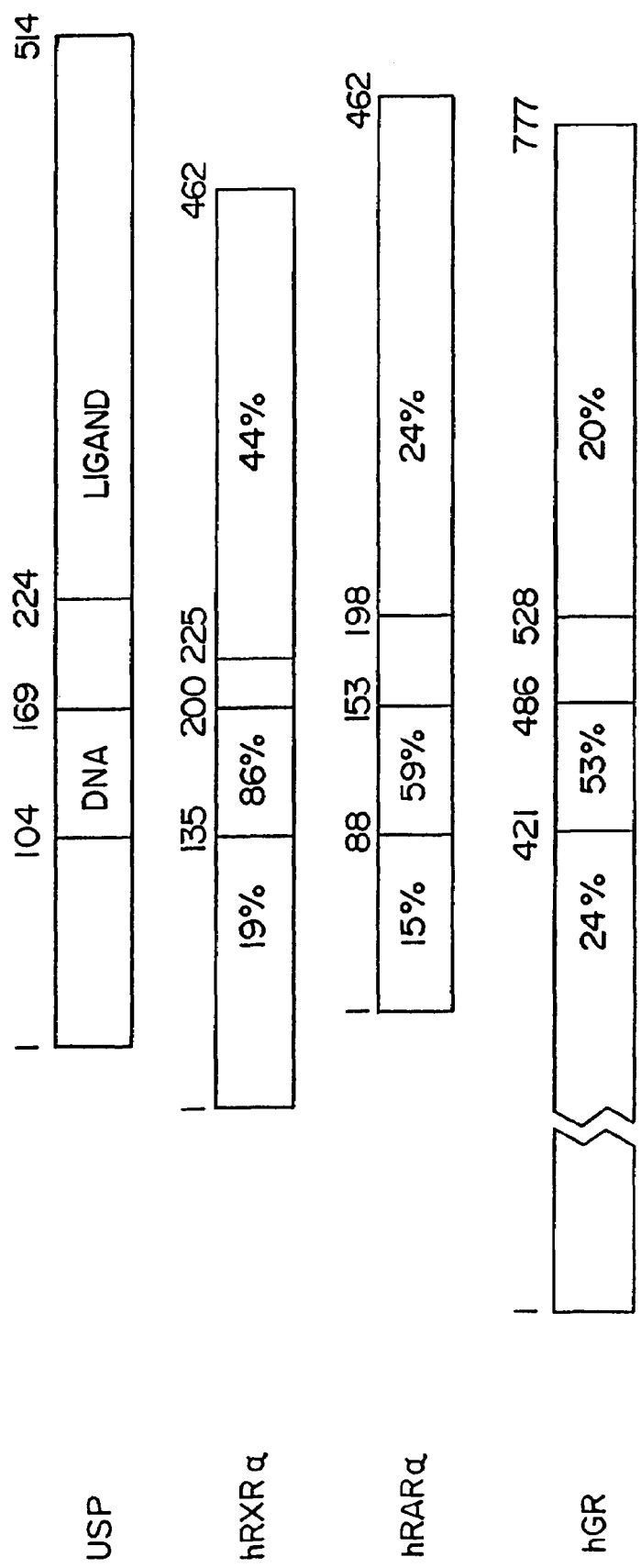
FIG. 1 presents a comparison of amino acid identity for various domains of invention ultraspiracle receptor (usp) in comparison with previously identified receptors human RXR-alpha (hRXRα), human retinoic acid receptor-alpha (hRARα) and human glucocorticoid receptor (hGR).

As employed herein, the term "ultraspiracle receptor" refers to a novel invertebrate polypeptide which has a DNA binding domain of about 66 amino acids with at least 9 Cys residues, more than about 75% amino acid identity in comparison with the DNA binding domain of hRXR-alpha (see Mangelsdorf et al., 1990, supra), less than about 60% amino acid identity in comparison with the DNA binding domain of hGR, and less than about 60% amino acid identify in comparison with the DNA binding domain of hRARα. Invention polypeptide can be further characterized by having less than 50% (but typically greater than 40%) amino acid identity in comparison with the ligand binding domain of hRXR-alpha, but less than 25% amino acid identity in comparison with the ligand binding domains of either hGR or hRARα. A sequence comparison of amino acid identity between invention receptor and several other receptors is presented in FIG. 1.

The deduced amino acid sequence for the ultraspiracle receptor is presented in SEQ ID NO:2 [see also, Oro et al., in Nature 347: 298–301 (1990)]. Also contemplated within the scope of the present invention are peptides comprising a DNA binding domain with substantially the same sequence as that of amino acids 104–169 shown in SEQ ID NO:2 (i.e., the DNA binding domain of the ultraspiracle receptor). As employed herein, the term "substantially the same amino acid sequence" refers to amino acid sequences having at least about 80% identity with respect to the reference amino acid sequence, and retaining comparable functional and biological properties characteristic of the protein encoded by the reference amino acid sequence. Preferably, proteins having "substantially the same amino acid sequence" will have at least about 90% amino acid identity with respect to the reference amino acid sequence; with greater than about 95% amino acid sequence identity being especially preferred. Also contemplated within the scope of the present invention are polypeptides having substantially the same sequence as that of amino acids 1–513 shown in SEQ ID NO:2. A presently preferred polypeptide of the invention is the polypeptide encoded by vector pXR2C8 [see Oro et al., supra].

As employed herein, the phrase "members of the steroid/thyroid superfamily of receptors" refers to all of the various isoforms of hormone binding proteins that operate as ligand-dependent transcription factors, including members of the steroid/thyroid superfamily of receptors for which specific ligands have not yet been identified (referred to hereinafter as "orphan receptors") Each such protein has the intrinsic ability to bind to a specific DNA sequence (i.e., regulatory sequence) associated with the target gene. The transcriptional activity of the gene is modulated by the presence or absence of the cognate hormone (ligand) as a result of binding of ligand to receptor, enabling interaction of receptor with the regulatory sequence.

The DNA-binding domains of all members of this superfamily of receptors are related, consisting of 66–68 amino acid residues, and possessing about 20 invariant amino acid residues, including nine cysteines. A member of the superfamily can be characterized as a protein which contains these diagnostic amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153), and the like. The highly conserved amino acids of the DNA-binding domain of members of the superfamily are as follows:

```
Cys - X - X - Cys - X - X - Asp* - X -

Ala* - X - Gly* - X - Tyr* - X - X -

X - X - Cys - X - X - Cys - Lys* - X -

Phe - Phe - X - Arg* - X - X - X - X -

X X X - X - X - (X - X -) Cys - X -

X - X - X - X - (X - X - X -) Cys - X -

X - X - Lys - X - X - Arg - X - X -

Cys - X - X - Cys - Arg* - X - X -

Lys* - Cys - X - X - X - Gly* - Met (SEQ ID No 3);
``` wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Exemplary members of the steroid/thyroid superfamily of receptors (including the various isoforms thereof) include steroid receptors such as glucocorticoid receptor, mineralocorticoid receptor, progesterone receptor, androgen receptor, vitamin $D_3$ receptor, and the like; plus retinoid receptors, such as the various isoforms of RAR (e.g., RARα, RARβ, or RARγ), the various isoforms of RXR (e.g., RXRα, RXRβ, or RXRγ), and the like; thyroid receptors, such as TRα, TRβ, and the like; insect derived receptors such as the ecdysone receptor, and the like; as well as other gene products which, by their structure and properties, are considered to be members of the superfamily, as defined hereinabove, including the various isoforms thereof (even though ligands therefor have not yet been identified; such receptors are referred to as "orphan receptors"). Examples of orphan receptors include HNF4 (see, for example, Sladek et al., in Genes & Development 4: 2353–2365 (1990)], the COUP family of receptors [see, for example, Miyajima et al., in Nucleic Acids Research 16: 11057–11074 (1988), and Wang et al., in Nature 340: 163–166 (1989)], COUP-like receptors and COUP homologs, such as those described by Mlodzik et al., in Cell 60: 211–224 (1990) and Ladias et al., in Science 251: 561–565 (1991), various isoforms of peroxisome proliferator-activated receptors (PPARs; see, for example, Issemann and Green, supra), the insect derived knirps and knirps-related receptors, and the like.

The formation of multimeric receptor(s) can modulate the ability of member(s) of the steroid/thyroid superfamily of receptors to trans-activate transcription of genes maintained under expression control in the presence of ligand for said receptor. The actual effect on activation of transcription (i.e., enhancement or repression of transcription activity) will vary depending on the receptor species which are part of the multimeric receptor, as well as on the response element with which the multimeric species interacts. Thus, for example, formation of a heterodimer of the ecdysone receptor with the ultraspiracle receptor promotes the ability of the ecdysone receptor to induce trans-activation activity in the presence of an ecdysone response element (see, for example, SEQ ID NO:26).

In accordance with another embodiment of the present invention, there is provided a method to modulate, in an expression system, the transcription activation of a gene by a member of the steroid/thyroid superfamily of receptors in the presence of ligand therefor, wherein the expression of said gene is maintained under the control of a hormone response element, said method comprising:

exposing said system to at least the dimerization domain of the ultraspiracle receptor, in an amount effective to form a multimeric complex receptor with said member of the steroid/thyroid superfamily of receptors.

Exposure of said system to at least the dimerization domain of the ultraspiracle receptor is accomplished by directly administering ultraspiracle receptor (or fragments thereof that allow modification of the receptor through the formation of heterodimeric receptor species) to said system, or by exposing said system to compound(s) and/or condition(s) which induce expression of the ultraspiracle receptor (or dimerization domain thereof). The resulting multimeric receptor species is effective to modulate transcription activation of said gene.

As employed herein, the term "modulate" refers to the ability of a given multimeric complex receptor to either enhance or repress the induction of transcription of a target gene by a given receptor, relative to such ability of said receptor in its uncomplexed state. The actual effect of multimerization on the transcription activity of a receptor will vary depending on the specific receptor species which are part of the multimeric complex receptor, and on the response element with which the multimeric complex receptor interacts. Thus, for example, formation of a heterodimer of the ecdysone receptor and the ultraspiracle receptor provides enhanced trans-activation activity with respect to the ability of the ecdysone receptor alone to promote trans-activation. Conversely, formation of a heterodimer of the ecdysone receptor and the dimerization domain of the ultraspiracle receptor should prevent the ability of ecdysone to promote trans-activation activity, since the resulting multimeric complex receptor will have a reduced ability to bind DNA, relative to the ability of ecdysone-usp multimeric complex to bind DNA.

The term "ecdysone" is employed herein in its generic sense (in accordance with common usage in the art), referring to compounds with the appropriate biological activity, in analogy with the terms estrogen or progestin [see, for example, Cherbas et al., in *Biosynthesis, metabolism and mode of action of invertebrate hormones* (ed. J. Hoffmann and M. Porchet), p. 305–322; Springer-Verlag, Berlin]. 20-Hydroxyecdysone is the major naturally occurring ecdysone. Analogs of the naturally occurring ecdysones are also contemplated within the scope of the present invention, such as for example, ponasterone A, 26-iodoponasterone A, muristerone, inokosterone, 26-mesylinokosterone, and the like.

As employed herein, the phrase "hormone response element" refers to short cis-acting sequences (i.e., having about 20 bp) that are required for hormonal (or ligand) activation of transcription. The attachment of these elements to an otherwise hormone-nonresponsive gene causes that gene to become hormone responsive. These sequences, commonly referred to as hormone response elements (or HREs), function in a position- and orientation-independent fashion. Unlike other enhancers, the activity of HREs can be modulated by the presence or absence of ligand. See, for example, Evans, Science 240: 889–895 (1988), and the references cited therein. In the present specification and claims, the term "hormone response element" is used in a generic sense to mean and embody the functional characteristics implied by all terms used in the art to describe these sequences.

Hormone response elements contemplated for use in the practice of the present invention include naturally occurring response elements as well as modified forms thereof (see, for example, SEQ ID NOs: 7, 12, 15, 25, 26, 28 and 29), as well as synthetic response elements which can be composed of two or more "half sites", wherein each half site comprises the sequence
-RGBNNM-,
wherein
R is selected from A or G;
B is selected from G, C, or T;
each N is independently selected from A, T, C, or G; and
M is selected from A or C;
with the proviso that at least 4 nucleotides of said -RG-BNNM- sequence are identical with the nucleotides at corresponding positions of the sequence -AGGTCA-, or the half-sites of ecdysone response elements (EcREs) (see, for example, SEQ ID NOs:26, 28 and 29) and
wherein the nucleotide spacing between each of said half-sites falls in the range of 0 up to 15 nucleotides, N.

When one of the half sites described above is incorporated into a synthetic response element in a direct repeat motif, and such half site varies by 2 nucleotides from the preferred sequence of -AGGTCA-, it is preferred that the other half site of the response element be the same as, or vary from the preferred sequence by no more than 1 nucleotide. It is presently preferred that the 3'-half site (or downstream half site) of a pair of half sites vary from the preferred sequence by at most 1 nucleotide.

When the above-described half sites are combined in direct repeat fashion (rather than as palindromic constructs), the resulting synthetic response elements are referred to as "DR-x", wherein "DR" refers to the direct repeat nature of the association between the half sites, and "x" indicates the number of spacer nucleotides between each half site.

Exemplary response elements useful in the practice of the present invention are derived from various combinations of half sites having sequences selected from, for example, -AGGTCA-, -GGTTCA-, -GGGTTA-, -GGGTGA-, -AG-GTGA-, -GGGTCA-, and the like.

The nucleotides employed in a non-zero spacer are independently selected from C, T, G, or A.

Exemplary three nucleotide spacers include -AGG-, -ATG-, -ACG-, -CGA-, and the like. Exemplary four nucleotide spacers include -CAGG-, -GGGG-, -TTTC-, and the like. Exemplary five nucleotide spacers include -CCAGG-, -ACAGG-, -CCGAA-, -CTGAC-, -TTGAC-, and the like.

Exemplary response elements contemplated by the present invention include the following DR-3 elements:
5'-AGGTCA-AGG-AGGTCA-3' (SEQ ID No. 4),
5'-GGGTGA-ATG-AGGACA-3' (SEQ ID No. 5),
5'-GGGTGA-ACG-GGGGCA-3' (SEQ ID No. 6), and
5'-GGTTCA-CGA-GGTTCA-3' (SEQ ID No. 7); the following DR-4 elements:
5'-AGGTCA-CAGG-AGGTCA-3' (SEQ ID No. 8),
5'-AGGTGA-CAGG-AGGTCA-3' (SEQ ID No. 9),
5'-AGGTGA-CAGG-AGGACA-3' (SEQ ID No. 10),
5'-GGGTTA-GGGG-AGGACA-3' (SEQ ID No. 11), and
5'-GGGTCA-TTTC-AGGTCC-3' (SEQ ID No. 12); the following DR-5 elements:
5'-AGGTCA-CCAGG-AGGTCA-3' (SEQ ID No. 13),
5'-AGGTGA-ACAGG-AGGTCA-3' (SEQ ID No. 14),
5'-GGTTCA-CCGAA-AGTTCA-3' (SEQ ID No. 15),
5'-GGTTCA-CCGAA-AGTTCA-3' (SEQ ID No. 16),
5'-AGGTCA-CTGAC-AGGGCA-3' (SEQ ID No. 17),
5'-GGGTCA-TTCAG-AGTTCA-3' (SEQ ID No. 18),
5'-AAGCTTAAG-GGTTCA-CCGAA-AGTTCA-CT-CAGCTT-3' (SEQ ID No. 19),
5'-AAGCTTAAG-GGTTCA-CCGAA-AGTTCA-CTCGCATAGCTT-3' (SEQ ID No. 20), and
5'-AAGCTTAAG-GGTTCA-CCGAA-AGTTCA-CTCGCATATATTAGCTT-3' (SEQ ID No. 21);
the ecdysone responsive elements set forth in SEQ ID NOs: 26, 28 and 29, and the like.

Presently preferred response elements contemplated for use in the practice of the present invention include:
5'-AGGTCA-AGG-AGGTCA-3' (SEQ ID No. 4),
5'-AGGTCA-CAGG-AGGTCA-3' (SEQ ID No. 8),
5'-AGGTGA-CAGG-AGGTCA-3' (SEQ ID No. 9),
5'-AGGTCA-CCAGG-AGGTCA-3' (SEQ ID No. 13),
5'-AGGTGA-ACAGG-AGGTCA-3' (SEQ ID No. 14),
SEQ ID NOs:26, 28, 29, and the like.

These are especially preferred because they represent synthetic and/or invertebrate sequences which have not been observed in vertebrates, and thus are applicable to a wide variety of reporter systems (i.e., the use of these response elements will not be limited due to any species preference based on the source of the sequence).

In accordance with yet another embodiment of the present invention, there is provided a method to modulate, in an expression system, the transcription activation of a gene by a member of the steroid/thyroid superfamily of receptors in the presence of ligand therefor, and in the further presence of the ultraspiracle receptor, wherein the expression of said gene is maintained under the control of a hormone response element, said method comprising:
exposing said system to compound(s) and/or condition(s) which prevent association of said member with the ultraspiracle receptor or fragments thereof, in an amount effective to prevent said association.

Compound(s) and/or condition(s) which prevent association of said member with the ultraspiracle receptor include hormone-like compounds which act as agonists or antagonists for the ultraspiracle receptor, antibodies raised against the dimerization domain of the ultraspiracle receptor, antibodies raised against the dimerization domain of said member, antisense sequence(s) based on sequence(s) complementary to known RNA encoding at least the dimerization domain of the ultraspiracle receptor, and the like. Amounts of agents effective to prevent such association will vary depending on the particular agents used and can be readily determined by those of skill in the art; typically falling in the sub-nanomolar up to micromolar range.

In accordance with still another embodiment of the present invention, there is provided a method for modulating the expression of an exogenous gene in a subject containing:
(i) a DNA construct encoding said exogenous gene under the control of a steroid or steroid-like hormone response element; wherein said response element is not normally present in the cells of said subject,
(ii) a receptor which is not normally present in the cells of said subject, wherein said receptor, in the presence of its associated ligand and the ultraspiracle receptor, binds to said steroid or steroid-like hormone response element, and
(iii) the ultraspiracle receptor;
said method comprising administering to said subject an effective amount of said associated ligand; wherein said ligand is not normally present in the cells of said subject; and wherein said ligand is not toxic to said subject.

As employed herein, the term "exogenous" (or "foreign") genes refers to both wild type genes and therapeutic genes, which are introduced into the subject in the form of DNA or RNA, either natural or synthetic. The gene of interest can be introduced into target cells (for in vitro applications), or the gene of interest can be introduced directly into a subject, or indirectly introduced by the transfer of transformed cells into a subject.

"Wild type" genes are those that are native to cells of a particular type, but which may be undesirably overexpressed in these cells, or may not be expressed in these cells in biologically significant levels. Thus, for example, while a synthetic or natural gene coding for human insulin would be exogenous genetic material to a yeast cell (since yeast cells do not naturally contain insulin genes), a human insulin gene inserted into a human skin fibroblast cell would be a wild type gene with respect to that cell since human skin fibroblasts contain the genetic material encoding human insulin, although human skin fibroblasts do not express human insulin in biologically significant levels.

Wild type genes contemplated for use in the practice of the present invention include genes which encode a gene product:
  the substantial absence of which leads to the occurrence of a non-normal state in said subject; or
  a substantial excess of which leads to the occurrence of a non-normal state in said subject;
  and the like.

As employed herein, the phrase "therapeutic gene" refers to genes which impart a beneficial function to the host cell in which such gene is expressed. Therapeutic genes are those that are not naturally found in host cells. For example, a synthetic or natural gene coding for authentic human insulin would be therapeutic when inserted into a skin fibroblast cell so as to be expressed in a host human, where the host human is not otherwise capable of expressing functionally active human insulin in biologically significant levels.

Therapeutic genes contemplated for use in the practice of the present invention include genes which encode a gene product:
  which is toxic to the cells in which it is expressed; or
  which imparts a beneficial property to said subject (e.g., disease resistance, etc);
  and the like.

Exogenous genetic material or genes useful in this embodiment of the present invention include genes that encode secretory proteins that can be released from said cell; enzymes that can metabolize a substrate from a toxic form to a benign form, or from a benign form to a useful form; regulatory proteins; cell surface receptors; and the like. Such useful genes include, but are not limited to, genes that encode blood clotting factors such as human factors VIII and IX; genes that encode hormones such as insulin, parathyroid hormone, luteinizing hormone releasing factor (LHRH), alpha and beta seminal inhibins, and human growth hormone; genes that encode proteins such as enzymes, the absence of which leads to the occurrence of an abnormal state in said subject; genes encoding cytokines or lymphokines such as interferons, granulocytic macrophage colony stimulating factor (GM-CSF), colony stimulating factor-1 (CSF-1), tumor necrosis factor (TNF), and erythropoietin (EPO); genes encoding inhibitor substances such as alpha$_1$-antitrypsin; genes encoding substances that function as drugs, e.g., genes encoding the diphtheria and cholera toxins; and the like.

Hormone response elements contemplated for use in this embodiment of the present invention involving modulating the expression of an exogenous gene in a subject include any sequence responsive to the above-described multimeric complex receptors, such as insect response elements, and the like. See, for example, SEQ ID NOs: 26, 28 and 29.

Insect response elements contemplated for use in modulating the expression of an exogenous gene in a subject according to the present invention include, for example, ecdysone response elements, and the like.

Such response elements are operably linked to a suitable promoter for expression of the target gene product. As used herein, the term "promoter" refers to a specific nucleotide sequence recognized by RNA polymerase, the enzyme that initiates RNA synthesis. This sequence is the site at which transcription can be specifically initiated under proper conditions. When exogenous genes, operatively linked to a suitable promoter, are introduced into the cells of a suitable host, the exogenous genes are subject to expression control in the presence of hormone or hormone-like compounds not normally present in the host cells. Exemplary promoters include ΔMTV, ΔSV, ΔADH promoters, and the like.

As employed herein, the phrase "receptor which is not normally present in the cells of said subject" refers to receptors which are not endogenous to the host in which the invention process is being carried out. Receptors which are not endogenous to the host include endogenous receptors modified so as to be non-responsive to ligands which are endogenous to the host in which the invention process is being carried out.

Receptor(s) not normally present in the cells of the subject and ultraspiracle receptor (or fragments thereof) can be provided to said subject by direct introduction of the proteins themselves, by introduction of RNA or DNA construct(s) encoding said receptors, by introduction of cells harboring genes encoding said receptor and/or response element, and the like. This can be accomplished in a variety of ways, e.g., by microinjection, retroviral infection, electroporation, lipofection, and the like.

As employed herein, the phrase "associated ligand" refers to a substance or compound which, inside a cell, binds to the receptor protein, thereby creating a ligand/receptor complex, which in turn can bind to an appropriate hormone response element. An associated ligand therefore is a compound which acts to modulate gene transcription for a gene maintained under the control of a hormone response element, and includes compounds such as hormones, growth substances, non-hormone substances that regulate growth, and the like. Ligands include steroid or steroid-like hormones, retinoids, thyroid hormones, pharmaceutically active compounds, and the like. Individual ligands may have the ability to bind to multiple receptors.

In accordance with a still further embodiment of the present invention, there is provided a method of inducing the expression of an exogenous gene in a subject containing:
  (i) a DNA construct encoding an exogenous gene product under the control of a hormone response element; wherein said response element is not normally present in the cells of said subject,
  (ii) DNA encoding a receptor which is not normally present in the cells of said subject, under the control of an inducible promoter; wherein said receptor, in the presence of its associated ligand and the ultraspiracle receptor, binds to said hormone response element,
  (iii) the ultraspiracle receptor, and
  (iv) the associated ligand for said receptor;
said method comprising subjecting a subject to conditions suitable to induce expression of said receptor.

In accordance with yet another embodiment of the present invention, there is provided a method of inducing expression of an exogenous gene product in a subject containing a DNA construct encoding said product under the control of a hormone response element; wherein said response element is not normally present in the cells of said subject, said method comprising introducing into said subject:

a receptor which is not normally present in the cells of said subject; wherein said receptor, in combination with its associated ligand and the ultraspiracle receptor, binds to a hormone response element, activating transcription therefrom, the ultraspiracle receptor, and the associated ligand for said receptor which is not normally present in the cells of said subject.

In accordance with this embodiment of the present invention, receptor can be provided directly to said subject as the protein, or indirectly by administering to said subject a second DNA construct encoding said receptor, or by administering to said subject cells harboring such constructs. When introduced as part of a second DNA construct, expression of said exogenous gene product and the receptor is preferably maintained under the control of a tissue specific promoter.

In accordance with a further embodiment of the present invention, there is provided a method for the expression of recombinant products detrimental to a host organism, said method comprising:

transforming suitable host cells with:

(i) a construct comprising a sequence encoding said recombinant product under the control of a hormone response element;

wherein said response element is not normally present in the cells of said host, and (ii) DNA encoding a receptor not normally present in said host cells;

growing said host cells to the desired level in the substantial absence of hormone(s) which, in combination with said receptor not normally present in the cells of said host and ultraspiracle receptor, is capable of binding to said hormone response element, and inducing expression of said recombinant product by introducing into said host cells the ultraspiracle receptor and hormone(s) which, in combination with said receptor not normally present in the cells of said host, bind to said response element.

In one aspect of this embodiment of the invention, wherein host is employed as an expression system for the production of a recombinant product which is toxic to the host, recombinant product is induced only after cell growth (as opposed to protein expression conditions) has produced a desired density of cell mass. Thus, the desired level of growth in accordance with this embodiment is a level which produces a high cell density, and thereafter expression of product is induced. Conditions suitable for cell growth (and for protein expression, when desired) can be readily determined by those of skill in the art.

In another aspect of this embodiment of the present invention, wherein the host harbors a DNA construct as described above, expression of the construct to produce the detrimental product causes ablation of the cells harboring said construct. In this aspect, the desired level of growth is that level appropriate to ensure the desired distribution of cells harboring the inducible construct. Thus, expression will be induced when it is desired to ablate such cells.

As used herein, "ablation" refers to removing or eliminating specific cell types in a culture of a cell population, or in a transgenic animal host by means of a DNA construct that encodes a protein whose presence is not per se toxic to the cells, but which can confer upon the cells a toxic potential due to the ability of the protein to control the expression of substances that are or will become toxic to the cells.

The elimination of specific cell-type(s) or specific cell line(s) in accordance with one aspect of the present invention produces a cell population which is substantially free of cells which are not normally present in the wild-type cell population. The elimination of specific cell-type(s) or specific cell line(s), in accordance with another aspect of the present invention, produces a defined altered state in the treated subject.

Cell(s) or cell line(s) contemplated to be eliminated in accordance with the present invention can be a cell or cell line capable of providing a desirable component to a cell population, as an exogenous gene product; wherein the ability to eliminate said cell or cell line from said cell population is desired, e.g., once said population achieves the ability to produce sufficient quantities of such component as an endogenous gene product; or, the cell line to be eliminated can be a diseased cell line or a cell line predisposed to a disease state.

Normal cell(s) or cell line(s) contemplated to be eliminated in accordance with the present invention are cell(s) or cell line(s), the elimination of which would result in the creation of a defined altered state in the cell population.

In accordance with a still further embodiment of the present invention, there is provided a method to distinguish the physiological effect of a first hormone receptor in a host from other hormone receptors in said host which respond to the same ligand, said method comprising:

replacing the ligand binding domain of said first receptor with a ligand binding domain from an exogenous receptor to produce a chimeric receptor maintained under the control of a tissue specific promoter;

wherein said exogenous receptor and the ligand to which the exogenous receptor responds are not normally present in said host; and wherein said exogenous receptor, in the presence of its associated ligand, binds to a hormone response element, thereby activating said response element, and thereafter monitoring the production of product(s) whose expression is controlled by said first hormone receptor when said host is exposed to ultraspiracle receptor and ligand to which said exogenous receptor responds.

In accordance with yet another embodiment of the present invention, there is provided a method to render a mammalian hormone receptor uniquely responsive to a ligand not endogenous to host(s) in which said receptor is normally found, said method comprising:

replacing the ligand binding domain of said receptor with a ligand binding domain from a second receptor;

wherein said second receptor is not normally present in said host; and wherein the ligand to which the second receptor responds is not normally present in said host.

In accordance with a still further embodiment of the present invention, there is provided a method to determine the ligand(s) to which orphan receptor(s) responds, said method comprising:

monitoring a host cell containing a reporter construct and a hybrid receptor for expression of product(s) of said reporter construct upon contacting said cell with potential ligands for said orphan receptor and the ultraspiracle receptor;

wherein said reporter construct comprises a gene encoding a reporter molecule, operatively linked for transcription to a steroid or steroid-like hormone response element; wherein said response element is not normally present in the cells of said host;

wherein said hybrid receptor comprises:

the N-terminal domain and DNA binding domain of a member of the steroid/thyroid superfamily of receptors, wherein said member is not normally present in the host cells, and wherein said member, in the presence of its associated ligand, binds said response element, activating transcription therefrom, and the ligand binding domain of said orphan receptor.

In accordance with yet another embodiment of the present invention, there is provided an isolated DNA which encodes the ultraspiracle receptor, as described above as well as functional fragments thereof. The complete nucleotide sequence for the ultraspiracle receptor is presented in SEQ ID NO:1 [see also, Oro et al., in Nature 347: 298–301 (1990)]. Also contemplated within the scope of the present invention are sequences encoding polypeptides comprising a DNA binding domain with substantially the same sequence as that of amino acids 104–169 shown in SEQ ID NO:2 (i.e., the DNA binding domain of the ultraspiracle receptor). Also contemplated are sequences encoding polypeptides having substantially the same sequence as that of amino acids 1–513 shown in SEQ ID NO:2. Also contemplated are sequences having substantially the same nucleotide sequence as nucleotides 163–1704 shown in SEQ ID NO:1. As employed herein, the term "substantially the same as" refers to DNA having at least about 70% homology with respect to the nucleotide sequence of the DNA fragment with which subject DNA is being compared. Preferably, DNA "substantially the same as" a comparative DNA will be at least about 80% homologous to the comparative nucleotide sequence; with greater than about 90% homology being especially preferred. Also contemplated are DNAs able to hybridize to the above-described sequences, and having substantially the same functional properties thereof. A presently preferred DNA of the invention is the EcoRI fragment of vector pXR2C8 [see Oro, et al., supra].

DNA of the invention can optionally be incorporated into expression vector(s) operative in a cell in culture to make the ultraspiracle receptor (or functional fragments thereof) by expression of said DNA in said cell. For example, the transcription of DNA can be controlled by the *Drosophila melanogaster* actin 5C promoter. Host cells which can employed for expression of said DNA include *Drosophila melanogaster* Schneider line 2 cells, Kc cells, and the like.

The invention will now be described in greater detail by reference to the following non-limiting examples.

EXAMPLES

Example I

Plasmids

CMX-EcR was constructed by digesting pActEcR plasmid [Koelle et al., Cell Vol. 67:59–77 (1991)] with HindIII. The resulting HindIII fragment, which contains the EcR coding region, was then inserted into CMXPL1, a derivative of CMX expression vector [Umesono et al. Cell Vol. 65:1255–1266 (1991)]. Expression plasmid CMX-usp was made by inserting the EcoRI fragment from the cDNA clone [Oro et al., Nature Vol. 347:298–301 (1990)] which contains all the usp coding region into CMXPL1 vector. ΔMTV-EcRE5-CAT was constructed by ligation of an EcRE-containing oligonucleotide (SEQ ID NO: 22):

```
5'-AGCTCGATGG ACAAGTGCAT TGAACCCTTG A
        GCTACC TGTTCACGTA ACTTGGGAAC TTCGA
``` into HindIII-cleaved ΔMTV-CAT [Hollenberg and Evans, Cell Vol. 55:899–906 (1988)]. Restriction analysis and sequencing of the construct indicated that it contains 5 copies of this oligonucleotide.

GEcR was constructed by ligation of a NotI/BamHI fragment containing the DNA and hormone binding domains of a modified EcR cDNA, EcRnx, in place of the DNA and hormone binding domains of the similarly modified glucocorticoid receptor expression construct pRSh-GRnx [Giguére et al., Nature Vol. 330:624–629 (1987)]. The modified receptor cDNA was constructed using the site-directed mutagenesis procedure of Kunkel, T. A., Proc. Natl. Acad. Sci. USA Vol. 82:448–492 (1985) to insert NotI (employing SEQ ID NO:23 as the oligonucleotide template) and XhoI (employing SEQ ID NO:24 as the oligonucleotide template) sites immediately flanking the DNA binding domain. SEQ ID NO:23 is:

5'-CCTGCGCCAC GGCGGCCGCC GGAGCTGTG CCTG; and SEQ ID NO:24 is:

5'-GTGGGTATG CGCCTCGAGT GCGTCGTCCC.

This mutagenesis procedure results in conversion of amino acids 258–260 from ValGlnGlu to ArgProPro and amino acid 331 from Pro to Leu.

Example II

Preparation of Receptor Protein, Cell Extracts and Gel Mobility Shift Assay

To generate protein in vitro, suitable plasmids for human (h)RARα, hTRB, hVDR, rat PPAR, *Drosophila* (d)usp and dEcR were linearized with restriction enzyme 3' of the termination codon. The linearized templates were used for in vitro transcription and then translation using rabbit reticulocyte lysate according to manufacturer's instruction (Promega). *Drosophila* embryo extract was a gift from Dr. J. Kadonaga and prepared as described by Zoeller et al., in Genes Dev., Vol. 2:68–81 (1988). Schneider cell extracts were prepared following the procedures in Damm et al., Nature Vol. 339:593–597 (1989) and Umesono et al. (1991), supra. The extraction buffer contained 0.4 M KCl in 20 mM HEPES pH 7.5, 20% glycerol, 2 mM DTT and 1 mM PMSF.

For gel mobility shift assay, proteins were incubated with binding buffer, which contained 100 mM KCl, 7.5% glycerol, 20 mM HEPES pH 7.5, 2 mM DTT and 0.1% NP-40, on ice for 20 minutes in the presence of 2 μg of nonspecific competitor poly dI-dC and other oligo competitors. Then approximately 1 ng of $^{32}$P-dCTP probe, which was labelled to specific activity about $1-5\times10^8$ cpm/μg by fill-in reaction with Klenow fragments, was added to the reaction and incubated at room temperature for 20 minutes. Antiserum or preimmune serum was added 10 minutes after the probe was added. The reaction was then loaded into 5% non-denaturing polyacrylamide gel in 0.5×TBE running buffer [1×TBE comprises 0.089 M Tris borate, 0.089 M boric acid and 0.002 M EDTA]. After electrophoresis, the gel was dried for autoradiography.

Example III

Preparation of usp Antiserum

Primers were designed to amplify the usp coding region which either covered the entire N-terminal and DNA binding domain (from amino acid 1 to 210; GST-uspN) or the complete coding region (GST-usp) by polymerase chain reaction (PCR). The amplified fragments were subcloned into PGEX2T vector (Pharmacia) for expression in bacteria. The expression of GST fusion protein was performed according to the manufacturer's directions (Pharmacia).

The fusion protein GST-uspN was prepared and fractionated on SDS polyacrylamide gel and the band corresponding to the fusion protein was excised. The gel slice was fragmented and used to immunize the rabbit at three week intervals. The rabbit sera were collected and tested by Western Blot for the ability to recognize usp protein. The positive sera were further purified by the procedure described in Vaughan et al., Met. in Enzymol. (Academic Press Vol. 168:588–617 (1989) with slight modification. Briefly, full length GST-usp fusion protein and GST protein were purified using Glutathione Sepharose 4B (Pharmacia). The purified proteins were individually coupled to affi-gel 10 according to the manufacturer's protocol (Biorad).

To affinity purify the antibody, the crude antiserum was first incubated with GST-coupled affi-gel for 2.5 hours at 4° C. with gentle rocking. The unbound fraction was separated from the beads by centrifugation. The supernatant was then incubated with full length GST-usp coupled affi-gel overnight at 4° C. with gentle rocking. The contents were then packed into column and washed with 50 mM HEPES pH 7.5 supplemented with 0.5 M NaCl. The bound antibodies were eluted by 100 mM glycine. The eluted fractions were neutralized with 1 M Tris pH 8 and pooled, then dialyzed against PBS buffer which contained 0.02% of sodium azide. The purified antiserum was concentrated by Centricon 30 (Amicon) before it was stored. This purified antibody is very specific as it does not cross react with RXRs. It also does not react with other closely related fly nuclear receptors including seven up (svp) type I, II [Mlodzik et al., Cell 60:211–224 (1990)].

Example IV

Cotransfection Assay

Transfection was performed with calcium-phosphate precipitation method as described previously [Umesono et al., Nature 336:262–264 (1989)]. CV1 monkey kidney cells were maintained in Dulbecco's modified Eagle's medium (DMEM) supplemented with 10% calf bovine serum. The cells were transfected for 8–9 hours and then the DNA precipitates were washed away and replaced with fresh medium with 10% charcoal-resin double stripped fetal bovine serum. 20-hydroxy-ecdysone (Sigma; 10 mg/ml in ethanol), or ethanol alone was then given to the cells. 24–28 hours later, the cells were harvested. Beta-galactosidase (βGal) activity was measured and a normalized amount of extract was used for CAT assay (Umesono et al. (1989) supra]. The following amount of plasmid DNA was included in the 10 cm plate transfection: 250 ng each of CMX-EcR and RSV-GEcR; 500 ng of CMX-usp; 5 µg ΔMTV-EcRE$_5$-CTA; 5 µg of βGal internal control plasmid CH111 (a derivative of CH110, Promega). The amount of CMX plasmid was kept constant in each transfection by adding CMX-luciferase. PGEM4 was added to bring the total amount of plasmid DNA to 15 µg per plate.

Example V usp is the *Drosophila* Nuclear Factor that can Enhance RAR DNA Binding Activity It has previously been shown that the DNA binding activity of bacterially expressed RAR can be enhanced by adding cell extracts to the binding reaction [Yang et al., Proc. Natl. Acad. Sci. USA 88:3559–3563 (1991)]. Extracts prepared from both mammalian cells and the *Drosophila* Schneider cell line 2 (S2) had similar effects [Yang et al., supra]. The presence of this enhancing activity in *Drosophila* cells indicates that a general conserved mechanism may be utilized in both mammals and *Drosophila* to regulate DNA binding activity of receptors like RAR. To address this question, experiments were set up to characterize this *Drosophila* nuclear activity in S2 cell extracts and in embryo extracts.

In gel mobility shift assays using a $^{32}$P-labelled natural RAR response element—βRARE [see SEQ ID NO:15, see also de The et al., in Nature Vol. 343:177–180 (1990); and Sucov et al., in Proc. Natl. Acad. Sci. USA Vol. 87:5392–5398 (1990)] as the probe, in vitro translated RARα was incubated with probe under binding conditions either alone or with 2 µg of S2 extracts or embryo extracts. In vitro translated RARα, by itself, did not bind with appreciable affinity. For mammalian extracts [Glass et al., Cell Vol. 63:729–738 (1990)], incubating the RARα with either S2 or *Drosophila* embryo extracts dramatically enhanced DNA binding activity, while cell extract alone did not show similar binding activity.

Two clues suggested the possibility that the observed enhancing activity might be the ultraspiracle receptor (usp). First, RXR, the putative vertebrate homologue of usp, has been shown to enhance RAR DNA binding [Yu et al., Cell Vol. 67:1251–1266 (1991); Kliewer et al., Nature Vol. 355:446–449 (1992); Leid et al., Cell Vol. 68:377–395 (1992)]. Second, usp protein has been found to be present in both S2 and embryo extracts with relative abundance. Based on these observations, it was investigated whether usp is the *Drosophila* nuclear activity that can interact with RAR. An affinity purified antibody against usp, prepared as described in Example III, was added to the mobility shift reaction. The affinity purified antibody supershifted the majority of the protein DNA complex while preimmune serum had no effect in the mobility pattern. By incubating with higher concentration of usp antibody, essentially all the binding complex was supershifted. These results indicate that the activity present in both types of fly extracts can be attributed to usp protein and that usp is likely the major factor in the extract which interacts with RAR.

To further show that usp is indeed the *Drosophila* component involved in the RAR interactions, usp protein was in vitro translated in the rabbit reticulocyte lysate (see Example II for procedure employed) and tested whether in vitro translated usp can mimic the fly extracts' activity to interact with RARα. Neither in vitro translated usp alone, nor RARα alone, bound to a βRARE probe. However, when the two proteins were incubated together, a prominent retarded complex appeared. This complex comigrated with the complex detected in the RAR and cell extract mixing experiments. The presence of both usp and RAR protein in this protein/DNA complex was demonstrated by the antibodies raised against usp and RARα. Either the affinity purified usp antibody, or the RARα, specifically affected the protein/ DNA complex, while preimmune sera had no effect. This complex likely represents an RAR/usp heterodimer, as its mobility is similar to the RXR/RAR complex which has been proposed to be a heterodimeric species [Yu et al., supra; Kliewer et al., supra; Leid et al., supra]. Thus it is concluded that usp is the *Drosophila* nuclear activity which can interact with RAR in binding to specific RARE via the formation of a putative heterodimer.

Example VI usp can Heterodimerize with Several Members of the Mammalian Nuclear Receptor Family The finding that usp is able to heterodimerize with RAR suggested that it would be appropriate to check whether this interaction reflected a general ability of usp to form heterodimers with other members of the steroid/thyroid superfamily. Using in vitro translated usp protein, interaction of usp with three mammalian nuclear receptors (TRβ, VDR and PPAR) was tested in gel mobility shift assays with the appropriate response element for each of the three receptors as the probes. Response elements used were as follows:

| Response Element | Abbreviation | Sequence | SEQ IN NO: |
|---|---|---|---|
| AOX-PPARE | (DR1)[1] | AGGACA A AGGTCA | 25 |
| SSP1-VDRE | (DR3)[2] | GGTTCA CGA GGTTCA | 7 |
| MLV-TRE | (DR4)[3] | GGGTCA TTTC AGGTCC | 12 |
| βRARE | (DR5)[4] | GGTTCA CCGAA AGTTCA | 15 |

[1]Kliewer et al., submitted to Nature, entitled "9-Cis Retinoic Acid and Peroxisome Proliferator Signalling Pathways Converge Through RXRα-PPAR Interactions"
[2]Noda et al., Proc. Natl. Acad. Sci. USA 87:9995–9999 (1990)
[3]Sap et al., Nature 340:242–244 (1989)
[4]Sucov et al., supra.

For a review providing further discussion with respect to these response elements, see Umesono et al., 1991, supra. With any of the receptors alone (prepared by in vitro translation from cDNA clones) there was very little or no binding to the test probes. However, when they were incubated with usp, a dramatic increase in DNA binding activity could be detected. In a usp dependent fashion, TRβ bound to a natural TR response element (MLV-TRE) and VDR/usp bound to SSP1-VDRE, a natural VDR response element. The usp and PPAR interaction was tested on a PPARE derived from the acyl CoA oxidase promoter (AOX, Kliewer et al., submitted, supra, and references cited therein). PPAR/usp complex bound to AOX-PPARE with high affinity. The usp antibody again showed the presence of usp in those complexes by shifting the retarded bands in all three combinations, whereas preimmune serum did not affect the binding pattern. Oligonucleotide competition assay demonstrated that the usp dependent heterodimers all showed correct response element specificity. Therefore, by interacting with usp to form heterodimer, all four mammalian receptors tested achieved high affinity DNA binding to their cognate response elements. It can be concluded, therefore, that the ability of usp to interact with other receptors to form heterodimers is a characteristic feature of usp, and that receptor heterodimer formation, as exemplified by RXR and usp, is conserved between vertebrates and invertebrates.

Example VII

Ecdysone Receptor and usp can Heterodimerize to Form a High Affinity DNA Binding Complex If the substitution of usp for RXR in heterodimerization with RAR and other mammalian receptors represents a conserved feature of mammalian and *Drosophila* receptors, it can be speculated that there might be one or more *Drosophila* activities which can interact with usp. The ligand binding domain has been shown to contain the dimerization domain for some nuclear receptors [Forman et al., Mol. Endocrinol. Vol. 3:1610–1626 (1989); Fawell et al., Cell 60:953–962 (1990)] and it is also essential for interaction between RAR and nuclear factors including RXR [Glass et al., supra; Kliewer et al. supra]. Sequence comparisons reveal that, with respect to the ligand binding domain, all RXR heterodimer partners, including RAR, TR and VDR, are much more similar to one another than to other receptors, particularly RXR. Among the *Drosophila* receptor members, ecdysone receptor (EcR) is one of the receptors which shows strong homology to RAR, VDR and TR within this region. This homology suggests EcR may have an evolutionarily conserved domain that, like RAR, VDR and TR, allows EcR to interact with usp.

To test the potential interaction between usp and EcR, experiments were carried out to determine whether usp is part of the defined EcR DNA binding activity present in ecdysone responsive Schneider 2 cells [Koelle et al. Cell 67:59–77 (1991)]. As shown by Koelle et al., in a gel mobility shift assay using a natural ecdysone response element derived from hsp27 promoter ($^{32}$P-labelled hsp27-EcRE, Riddihough and Pelham, EMBO J. Vol. 6:3729–3734 (1987)] as the probe, one specific major complex could be detected in the S2 extract. This complex can be competed away by specific cold oligonucleotide but not by the unrelated oligonucleotide competitor GREpal, a glucocorticoid response element. To determine whether usp is present in this EcRE binding complex, affinity purified usp antibody was added to the reaction. usp antibody can supershift the specific EcRE binding complex from the S2 extract but not the lower minor complex, which was much less sensitive to the specific cold oligonucleotide competition. Preimmune serum had no effect on the upper major complex but it disrupted the lower minor complex. Antibody against RXRα and RARγ did not affect the specific complex. Therefore, these data demonstrate that usp is part of the EcRE DNA binding complex present in S2 cells, strongly suggesting an interaction between EcR and usp.

The EcR and usp interaction was also tested under more defined conditions. In vitro translated EcR and usp were prepared and their interaction was assayed by gel mobility shift assays. Using the same hsp27-EcRE as the probe, usp did not bind to this element by itself. EcR also failed to bind to hsp27-EcRE, in contrast to the EcRE binding activity in S2 cells. To test whether usp can complement EcR DNA binding, as it does with mammalian receptors, both usp and EcR were co-incubated in the reaction. In the presence of both receptors, a novel high affinity DNA binding complex appeared. Usp antibody, but not preimmune serum, can supershift the complex, demonstrating that usp is part of the complex. This complex is proposed to be a heterodimeric species, which is consistent with the observation of other usp heterodimers. These data demonstrate that EcR binding to ecdysone response element (hsp27-EcRE) depends upon usp and are consistent with the existence of a functionally significant EcR/usp complex.

Example VIII

DNA Binding Activity of EcR/usp Heterodimer is Correlated with the Ecdysone Responsiveness In Vivo To establish that the EcR/usp heterodimer is physiologically relevant, it was set out to determine whether the DNA binding properties of EcR/usp heterodimer can be correlated with ecdysone responsiveness in vivo. This was done by testing EcR/usp heterodimer binding to several wild type and mutant EcREs characterized by their differential ability to mediate the ecdysone responsiveness in cultured cells (for review see Cherbas et al., Genes Dev. Vol. 5:120–131 (1991)). The response elements used in this study are set forth below. The position and the orientation of ERE-like half sites (AGGTCA-like) are marked by arrows. For example, the palindromic motif in hsp27-EcRE is indicated by arrows arranged as → ←. The mutated nucleotides in 11N and 15N-EcRE are in small letters. The arrow in 11N-EcRE covers where the remaining palindromic motif extends. In Eip28/29-EcRE, which is named as dis*-Eip28/29 in Cherbas et al., supra, the half site which can constitute a highly degenerated palindrome is marked with a wavy, broken line. Note that two ERE half sites are present in the configuration of direct repeats spaced by three nucleotides in Eip28/29-EcRE. The ability of individual response elements to mediate ecdysone response in cultured cells (summarized from Cherbas et al., supra) and to serve as high affinity binding site for EcR/usp complex are summarized to the right of the sequences.

high affinity binding by the EcR/usp complex parallels the ability the Eip28/29-EcRE to mediate ecdysone response in culture cells.

In contrast to the high affinity binding referred to above, a mutant hsp27-EcRE (referred as 11-N-hsp by Cherbas et al., supra, wherein the two nucleotides at the ends of the palindrome and the flanking sequence were changed), failed to serve as a high affinity binding site for the EcR/usp. This oligonucleotide did not compete the specific binding of EcR/usp to hsp27-EcRE, which was consistent with the observation that this mutated EcRE failed to confer ecdysone responsiveness to a heterologous promoter in transfection assay (Cherbas et al., supra). However, a back mutation which regenerated the palindrome motif (15-N-hsp) led to recovery of the ecdysone responsiveness and effective competition for the EcR/usp binding to the wild type hsp27-EcRE. Therefore, the ability of a specific EcRE motif to mediate the ecdysone response in vivo correlated well with its ability to serve as high affinity binding site for EcR/usp complex. These data suggest that the EcR/usp complex can mediate the ecdysone response in vivo.

Example IX usp is Present in the Embryonic EcRE Binding Activity

Phenotypic analysis of usp reveals that it is required at a number of developmental events which are correlated with known or potential ecdysone-regulated processes. For example, usp is found to be a necessary component for the

|  |  | Ability to Mediate Ecdysone Response | Ability to Function as Binding Site for EcR/usp Multimeric Complex |
|---|---|---|---|
| hsp27-EcRE (SEQ ID NO:26) | -----><br>ATTGGACAAGTGCATTGAACCCTTGTCTCT<br>TAACCAGTTCACGTAACTTGGGAACAGAGA<br>       <----- | + | + |
| 11N-EcRE (SEQ ID NO:27) | ----><br>atgctGTGCATTGAACgtgctcga<br>tacgaCACGTAACTTGcacgagct<br>     <---- | – | – |
| 15N-EcRE (SEQ ID NO:28) | -----><br>atgAAGTGCATTGAACCCgctcga<br>tacTTCACGTAACTTGGGcgagct<br>   <----- | + | + |
| Eip28/29-EcRE (SEQ ID NO:29) | -----><br>TAAAGGATCTTGACCCCAATGAACTTCTTA<br>ATTTCCTAGAACTGGGGTTACTTGAAGAAT<br>       <-----   <----- | + | + |

An EcRE derived from the *Drosophila* Eip28/29 gene has been shown to mediate ecdysone response in cultured cells [Cherbas et al., supra]. In contrast to the hsp27-EcRE palindrome, the Eip28/29-EcRE is a composite element containing a direct repeat and a highly degenerated palindromic motif. The ability of EcR/usp complex to recognize this EcRE was examined. This element can effectively compete the EcR/usp binding to hsp27-EcRE. This competition is as effective as that of the hsp27-EcRE itself, demonstrating that the Eip28/29-EcRE is also a high affinity binding site for EcR/usp complex. In contrast, an unrelated competitor (GREpal) had no effect on the DNA binding. The completion of embryogenesis [Oro et al., "The *Drosophila* retinoid X receptor homolog ultraspiracle functions in both female reproduction and eye morphogenesis", Development, in press (1992)]. The presence of the ecdysone pulse [Richards, G., Mol. and Cell. Endocrinol. Vol. 21:181–197 (1981)] as well as the EcR protein (Koelle et al., supra) during embryogenesis indicates that EcR is also required during embryonic development.

Based on the coexpression and functional requirement of both activities, it was next tested whether EcR and usp can interact during this developmental stage. To this end, the EcRE binding activities in the embryo extract were determined by mobility shift assay using 5–10 µg of embryo extract and $^{32}$P-labelled hsp27-EcRE as the probe. Specific EcRE binding complexes can be detected, as demonstrated by specific oligonucleotide and unrelated oligonucleotide competition. Indeed, usp is present in those complexes, as usp antibody was able to supershift those complexes. Preimmune serum did not alter the mobility pattern, although a slightly enhanced overall DNA binding was observed. The detection of multiple EcRE binding complexes is consistent with the existence of multiple forms of EcR protein which have been reported (Koelle et al., supra). The identities of these complexes as EcR complexes were supported by the fact that the upper complex comigrated with the EcR complex present in the S2 extract and that the DNA binding specificity of these complexes as assayed by oligonucleotide competition was indistinguishable from the EcR/usp complex prepared in vitro.

Based on these data, it can be concluded that the embryonic EcRE binding complexes contain usp. These data suggest an interaction between endogenous usp and EcR in the *Drosophila* embryo, where both activities are required for embryonic development.

Example X usp is Required for Ecdysone Responsiveness in Heterologous Cultured Cells The in vitro DNA binding data suggests that usp is required for EcR high affinity DNA binding. The detection of EcR/usp heterodimeric DNA binding complex from embryo implies that they may interact in vivo. To determine whether usp and EcR can functionally interact in vivo, cotransfection experiments were set up to assay if usp is required for EcR to exert an ecdysone response in cultured cells. Mammalian cells were chosen as the heterologous system because they do not contain endogenous EcR and usp background.

Ecdysone response in CV1 cells was determined by using an ecdysone-responsive reporter gene (ΔMTV-EcRE$_5$-CAT), which contains the same core hsp27-EcRE motif tested in DNA binding assay described earlier. The chloramphenicol acetyl transferase (CAT) activity induced by ecdysone was measured in the presence of different combinations of transfected EcR and usp expression vectors. CAT activity is expressed in FIG. 2 as the percentage of conversion which is normalized against the level in EcR alone at the presence of ecdysone assigned as one (column 1, shaded rectangle). The final concentration of 20-hydroxy-ecdysone (Sigma) is 40 μM. Columns 1 and 2 show that transfection with EcR alone (column 1) or usp alone (Column 2) does not respond to 20-OH-ecdysone treatment. Cotransfection of EcR and usp together is shown in column 3 and the induction of CAT activity could be observed by about 3 fold. The requirement of EcRE for induction is demonstrated by using the parental ΔMTV-CAT as reporter. This construct does not respond to ecdysone (column 4).

Figure 2A:
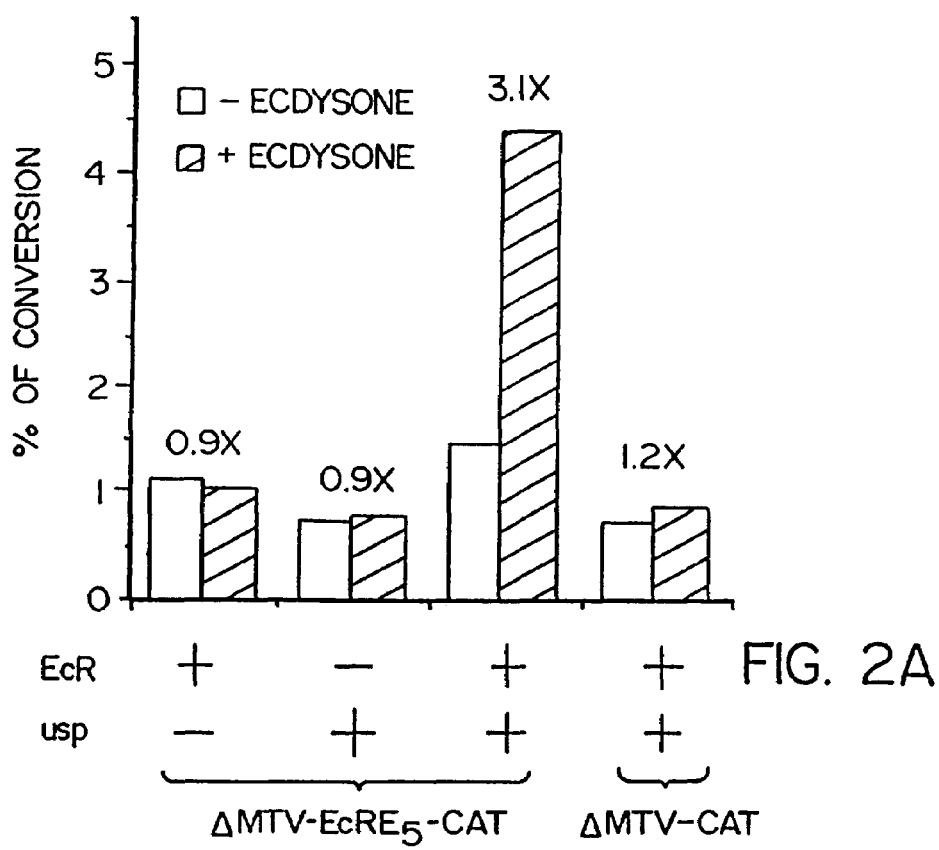
FIG. 2 presents the % conversion of substrate by chloramphenicol acetyltransferase (CAT) as a result of cotransfection of mammalian (CV1) cells with ecdysone receptor (EcR) encoding vector and/or ultraspiracle receptor (usp) encoding vector along with CAT reporter vector which contains an ecdysone response element (EcRE).

As shown in FIG. 2A, transfection of EcR alone failed to confer responsiveness to 20-hydroxy-ecdysone, consistent with the idea that EcR by itself cannot mediate ecdysone response. To test whether usp can complement the EcR activity as it did in the DNA binding assay, usp expression vector was cotransfected with EcR into CV1 cells. Cotransfection of usp with EcR indeed was able to confer a significant response to 20-OH-ecdysone (over 3 fold, FIG. 2A). This induction was strictly dependent on both EcR and EcRE, as transfection with usp expression plasmid alone or a reporter construct without EcRE (ΔMTV-CAT) did not result in ecdysone responsiveness (FIG. 2A). The level of induction by EcR and usp in CV1 cells is significant but somewhat lower than expected compared with the interaction in DNA binding assay.

To address the possibility that EcR may not function properly in mammalian cells, the N-terminal domain of the glucocorticoid receptor (GR) was fused to the EcR DNA binding domain and ligand binding domain to create the construct GEcR (see Example 1). The presence of the GR N-terminal domain, which contains a transactivating domain [Hollenberg and Evans, supra], should increase the transcriptional potency and provide an optimal translation signal for *Drosophila* EcR protein to function properly in the mammalian cells. This construct retained the ability to interact with usp in DNA binding assay. Since usp did not interact with GR in either DNA binding or in transfection assay, it is clear that GR N-terminal fusion should not affect the basic property of EcR to interact with usp. A similar GR fusion protein with TR has been shown to behave like wild type TR except that it is a more potent transactivator [Thompson and Evans, Proc. Natl. Acad. Sci. USA Vol. 86:3494–3498 (1989)]. Therefore this system should increase the sensitivity of a functional interaction between usp and EcR while faithfully retaining the basic property of EcR.

Figure 2B:
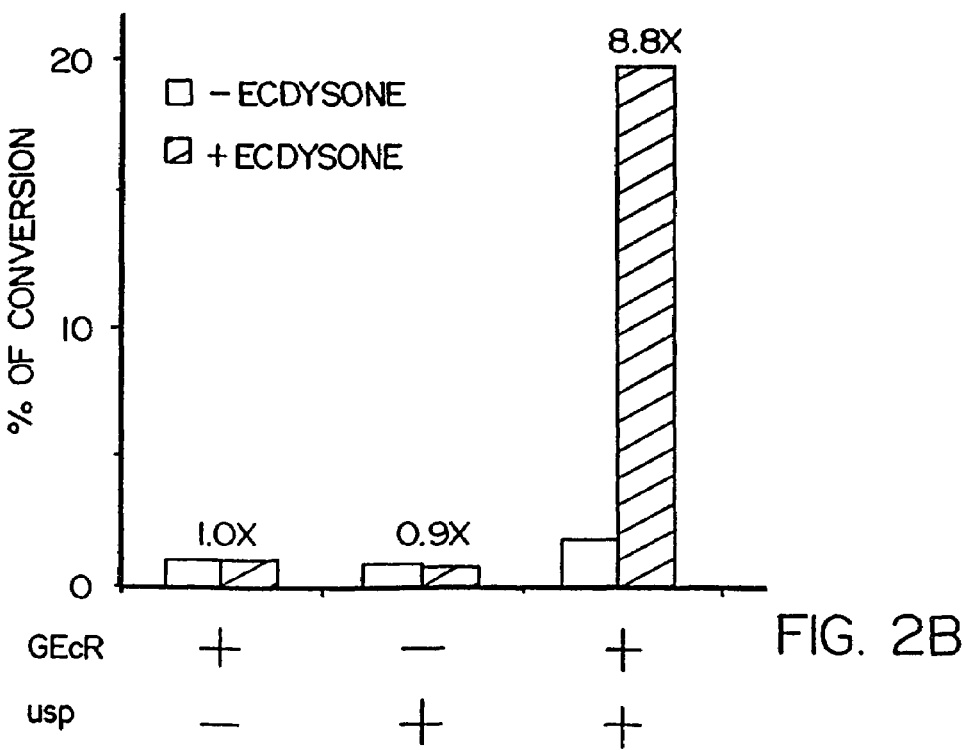

As shown in FIG. 2B, expression plasmid of GEcR was transfected into CV1 cells alone, or with usp expression plasmid. The conversion of CAT was normalized as described for panel A. Note that the scales of the CAT conversion in FIG. 2, panels A and B are different. Similar to the results obtained with wild type EcR, transfection of GEcR alone failed to confer ecdysone response. However, when cotransfected with the usp expression plasmid, the 20-OH-ecdysone treatment induced CAT activity by 8–10 fold (FIG. 2B). This induction was also dependent on the presence of the EcRE in the reporter constructs. Thus, the GEcR mediated ecdysone response is similar to EcR except the signal level is higher (compare FIGS. 2A and 2B). In conclusion, the presence of usp appears to be essential for EcR and GEcR to exert an ecdysone response in CV1 cells. These data demonstrate that EcR and usp can interact in vivo and constitute a functional ecdysone response in a heterologous cell line.

While the invention has been described in detail with reference to certain preferred embodiments thereof, it will be understood that modifications and variations are within the spirit and scope of that which is described and claimed.

The invention claimed is:

1. A method for modulating the expression of an exogenous gene in a subject containing:
   (i) a DNA construct encoding said exogenous gene under the control of a steroid or steroid-like hormone response element; wherein said response element is not normally present in the cells of said subject,
   (ii) a receptor which is not normally present in the cells of said subject, wherein said receptor, in the presence of its associated ligand and the ultraspiracle receptor, binds to said steroid or steroid-like hormone response element, and
   (iii) ultraspiracle receptor;
   said method comprising administering to said subject an effective amount of said associated ligand; wherein said ligand is not normally present in the cells of said subject; and wherein said ligand is not toxic to said subject.

2. A method according to claim 1 wherein said receptor not normally present in the cells of the subject and said ultraspiracle receptor are provided to said subject by DNA construct(s) encoding said receptors.

3. A method according to claim 2 wherein said receptors are expressed under the control of a tissue specific promoter.

4. A method according to claim 1 wherein said exogenous gene is selected from the group consisting of a gene naturally contained in the genome of said subject, and a gene not naturally contained in the genome of said subject.

5. A method according to claim 4 wherein said wild type genes are selected from genes which encode gene products:
   the substantial absence of which leads to the occurrence of a non-normal state in said subject; or
   a substantial excess of which leads to the occurrence of a non-normal state in said subject.

6. A method according to claim 4 wherein said therapeutic genes are selected from those which encode gene products:
   which are toxic to the cells in which they are expressed; or
   which impart a beneficial property to said subject.

7. A method of inducing the expression of an exogenous gene in a subject containing:
   a) a DNA construct encoding an exogenous gene product under the control of a hormone response element; wherein said response element is not normally present in the cells of said subject,
   b) DNA encoding a receptor which is not normally present in the cells of said subject, under the control of an inducible promoter; wherein said receptor, in the presence of its associated ligand and the ultraspiracle receptor, binds to said hormone response element,
   c) ultraspiracle receptor, and
   d) the associated ligand for said receptor which is not normally present in the cells of said subject,
   said method comprising subjecting a subject to conditions suitable to induce expression of said receptor which is not normally in the cells of said subject.

8. A method according to claim 7, wherein said ultraspiracle receptor is provided to said subject by a DNA construct encoding said ultraspiracle receptor.

9. A method according to claim 8, wherein said receptors are expressed under the control of a tissue-specific promoter.

10. A method according to claim 7, wherein said ultraspiracle receptor is substantially the same as that set forth in amino acids 1–513 of SEQ ID NO:2.

11. A method according to claim 7, wherein said exogenous genes are wild type genes or therapeutic genes.

12. A method according to claim 11, wherein said wild type genes encode gene products:
   a) the substantial absence of which leads to the occurrence of a non-normal state in said subject, or
   b) a substantial excess of which leads to the occurrence of a non-normal state in said subject.

13. A method according to claim 11, wherein said therapeutic genes encode gene products:
   a) which are toxic to the cells in which they are expressed, or
   b) which impart a beneficial property to said subject.

14. A method of inducing expression of an exogenous gene product in a subject containing a DNA construct encoding said product under the control of a hormone response element; wherein said response element is not normally present in the cells of said subject, said method comprising introducing into said subject:
   a) a receptor which is not normally present in the cells of said subject;
   wherein said receptor, in combination with its associated ligand and ultraspiracle receptor, binds to said hormone response element, activating transcription therefrom,
   b) the ultraspiracle receptor, and
   c) the associated ligand for said receptor.

15. A method according to claim 14, wherein said receptor not normally present in the cells of said subject and said ultraspiracle receptor are provided to said subject by DNA construct(s) encoding said receptors.

16. A method according to claim 15, wherein said receptors are expressed under the control of a tissue-specific promoter.

17. A method according to claim 14, wherein said ultraspiracle receptor is substantially the same as that set forth in amino acids 1–513 of SEQ ID NO:2.

18. A method according to claim 14, wherein said exogenous genes are wild type genes or therapeutic genes.

19. A method according to claim 18, wherein said wild type genes encode gene products:
 a) the substantial absence of which leads to the occurrence of a non-normal state in said subject, or
 b) a substantial excess of which leads to the occurrence of a non-normal state in said subject.

20. A method according to claim 18, wherein said therapeutic genes encode gene products:
 a) which are toxic to the cells in which they are expressed, or
 b) which impart a beneficial property to said subject.

* * * * *